US008265886B2

(12) United States Patent
Bisiaux et al.

(10) Patent No.: US 8,265,886 B2
(45) Date of Patent: *Sep. 11, 2012

(54) NON-DESTRUCTIVE TESTING, IN PARTICULAR FOR PIPES DURING MANUFACTURE OR IN THE FINISHED STATE

(75) Inventors: Bernard Bisiaux, Valenciennes (FR); Frédéric Lesage, Saint-Saulve (FR); Sébastien Petit, Thumeries (FR); Sylvain Deutsch, Semur en Auxois (FR)

(73) Assignee: V & M France, Boulogne-Billancourt (FR)

( * ) Notice: Subject to any disclaimer, the term of this patent is extended or adjusted under 35 U.S.C. 154(b) by 733 days.

This patent is subject to a terminal disclaimer.

(21) Appl. No.: 12/306,534

(22) PCT Filed: Jun. 25, 2007

(86) PCT No.: PCT/FR2007/001048
§ 371 (c)(1),
(2), (4) Date: Feb. 4, 2009

(87) PCT Pub. No.: WO2008/000940
PCT Pub. Date: Jan. 3, 2008

(65) Prior Publication Data
US 2009/0301202 A1 Dec. 10, 2009

(30) Foreign Application Priority Data
Jun. 30, 2006 (FR) .................................... 06 05923

(51) Int. Cl.
*G01N 29/06* (2006.01)
*G01N 29/26* (2006.01)
(52) U.S. Cl. .............. 702/39; 73/592; 73/638; 73/644; 73/622; 73/623

(58) Field of Classification Search .................. 702/39
See application file for complete search history.

(56) References Cited

U.S. PATENT DOCUMENTS
4,625,557 A * 12/1986 Rutherford ................... 73/635
(Continued)

FOREIGN PATENT DOCUMENTS
FR 2 796 153 1/2001
(Continued)

OTHER PUBLICATIONS
Terada, Atsuhiko; Ultrasonic Flaw Detection Evaluating Device; May 1998; English abstract for JP-115604A.*
(Continued)

*Primary Examiner* — Sujoy Kundu
*Assistant Examiner* — Haidong Zhang
(74) *Attorney, Agent, or Firm* — Oblon, Spivak, McClelland, Maier & Neustadt, L.L.P.

(57) ABSTRACT

A non-destructive testing device for pipes is provided. The device extracts information on defects from signals captured by ultrasound receivers following the selective excitation of ultrasound transmitters according to a selected time rule. The receivers form an arrangement with a selected geometry, coupled in an ultrasound fashion, with relative rotation/translation movement, with the pipe. The device includes a converter that selectively isolates a digital representation of echoes in designated time windows, as a function of the movement, and by extracting an image of defects, a filter which determines presumed defect zones and properties of these, a combiner to prepare working digital inputs from an extract of images of a defect zone, a neural circuit receiving the working inputs, a digital decision and alarm stage working on the basis of the output of the neural circuit, and a sorting and marking robot.

15 Claims, 16 Drawing Sheets

U.S. PATENT DOCUMENTS

2005/0156364 A1* 7/2005 Bisiaux et al. .............. 266/79
2010/0307249 A1 12/2010 Lesage et al.

FOREIGN PATENT DOCUMENTS

| JP | 10115604 A | * | 5/1998 |
| JP | 10311138 A | * | 11/1998 |
| WO | 95 03526 | | 2/1995 |

OTHER PUBLICATIONS

Terada, Atsuhiko; Ultrasonic Flaw Detection Evaluating Device; May 1998; English translation for JP-115604A.*

Seki, Munemasa; Construction for Identifying single Pipe; Nov. 1998; English abstract for JP-10311138A.*

Seki, Munemasa; Construction for Identifying single Pipe; Nov. 1998; English translation for JP-10311138A.*

Ravanbod, et al., "Application of neuro-fuzzy techniques in oil pipelione ultrasonic nondestructive testing" NDT&E International, vol. 38, No. 8, pp. 643-653, XP005058825 (2005).

Dunlop, I. et al., "Shape classification of flaw indications in three-dimensional ultrasonic images", IEEE Proc.-Sci. Meas. Technol., vol. 142, No. 4, pp. 307-312, XP006004423 (1995).

Margrave, F. et al., "The use neural networks in ultrasonic flaw detection", Measurement, vol. 25, No. 2, pp. 143-154, XP004158745, (1999).

U.S. Appl. No. 12/808,915, filed Jun. 17, 2010, Lesage, et al.

* cited by examiner

TYPE 2
Angle 0°

TYPE 4
Angle 20 – 80°

TYPE 1
Angle 0°

TYPE 3
Angle 20 – 80°

NON-DESTRUCTIVE TESTING, IN PARTICULAR FOR PIPES DURING MANUFACTURE OR IN THE FINISHED STATE

The invention concerns the non-destructive testing of materials, especially for pipes in the process of manufacture.

Various options, more of which later, are known which tend to use neural networks in connection with non-destructive testing of materials. But those currently in existence are unable to operate in an industrial environment, on equipment already in service, in real time, whilst allowing a classification on the fly of imperfections according to their type, in such a way that it is possible to quickly remedy a problem, arising during the production phase.

The object of the invention is to improve the situation by moving towards a system that:
- can be used in an industrial environment and can be easily installed on equipment that already exists in this environment;
- can be used in real time, that is to say can provide rapid diagnosis (at a speed that is fast enough not to slow down the overall speed of production), and
- allows a classification of imperfections according to their type in order to know their severity and a determination of the technical reason for the imperfection, as well as the rapid remedying of the problem during the production phase.

According to an initial aspect of the invention, a device is proposed that forms an operating tool for the non-destructive testing of pipes (or other iron and steel products) during and at the end of production. Such a tool is intended to extract information on possible imperfections in the pipe. Transmitting ultrasound sensors are excited selectively according to a selected time rule. Feedback signals are captured by receiving ultrasound sensor forming an arrangement with a selected geometry, mounted in ultrasound coupling with the pipe via the intermediary of a liquid medium. Finally, there is generally a relative rotation/translation movement between the pipe and the transducer arrangement.

The operating tool proposed comprises:
- a converter, capable of selectively isolating a digital representation of possible echoes in designated time windows, as a function of the relative rotation/translation movement, and extracting from this an image of possible imperfections in the pipe;
- a filter, capable of determining, in the images, presumed imperfection zones, as well as the properties of each presumed imperfection;
- a combiner, arranged to prepare digital inputs for the neural circuit, from an extract of the images corresponding to a presumed imperfection zone, properties of the presumed imperfection in the same zone, coming from the filter, and contextual data;
- at least one neural circuit that receives the inputs from the combiner;
- a decision and alarm digital stage, operating on the basis of the output from the neural circuit, and
- a sorting and marking robot, arranged to separate and mark pipes that have been deemed not to conform by the decision and alarm digital stage.

The invention is equally at home as a non-destructive testing device for pipes (or other iron and steel products) during or at the end of production, which comprises:
- an arrangement of ultrasound transducers with a selected geometry, mounted in ultrasound coupling with the pipe via the intermediary of a liquid medium, with relative rotation/translation movement between the pipe and the transducer arrangement;
- circuits to selectively excite these transducer elements according to a selected time rule, and for gathering the feedback signals they capture, and
- an operating tool as defined above and detailed in the following.

Another aspect of the invention manifests itself in the form of a non-destructive testing procedure for pipes (or other iron and steel products) during or at the end of production, comprising the following stages:
a. providing an arrangement of ultrasound transducers with a selected geometry, mounted in ultrasound coupling with the pipe via the intermediary of a liquid medium, with relative rotation/translation movement between the pipe and the transducer arrangement;
b. selectively exciting these transducer elements according to a selected time rule;
c. gathering the feedback signals they capture, in order to selectively analyse these feedback signals, so as to extract information on any imperfections in the pipe.

The proposed procedure also comprises the following stages:
d. selectively isolating a digital representation of possible echoes in designated time windows, as a function of the relative rotation/translation movement, and extracting from this an image of possible imperfections in the pipe;
e. filtering the images according to selected filter criteria, in order to determine presumed imperfection zones there, and the properties of each presumed imperfection;
f. forming digital inputs for the neural circuit, from an extract of the images corresponding to a presumed imperfection zone, properties of the presumed imperfection in the same zone, coming from the filter, and contextual data;
g. applying the inputs so formed to at least one neural circuit;
h. digitally processing the output of the neural circuit according to selected decision criteria, in order to extract from this a decision and/or an alarm, and
i. separating and marking pipes considered not to conform by stage h.

Other aspects of the invention will be found in the remainder of this patent application.

Other characteristics and advantages of the invention will become apparent upon examination of the detailed description that follows and the attached drawings, in which.

Figure 1:
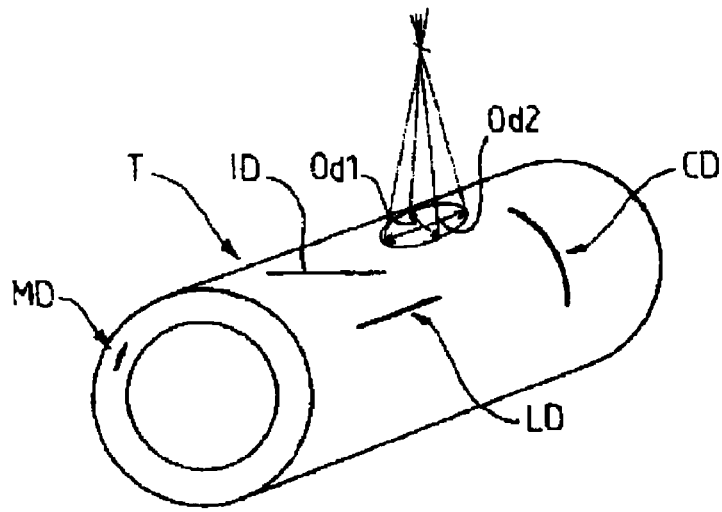
FIG. 1 is a schematic perspective view of a pipe with imperfections or defects so-called reference imperfections or reference defects.

The drawings contain elements of a definite nature. They can therefore not only serve to better understand the present invention but can also contribute to its definition, as necessary.

In the remainder of this text, an ultrasound sensor may be referred to without distinction as a sensor, or probe or transducer, all of which are well-known to a person skilled in the art.

Known Uses of Neural Networks

The use of neural networks in connection with non-destructive testing of materials has been the subject of numerous publications, mostly quite theoretical, which will be considered now.

The article entitled 'Localization and Shape Classification of Defects using the Finite Element Method and the Neural Networks' by ZAOUI, MARCHAND and RAZEK (NDT-.NET—AUGUST 1999, Vol. IV, abridged Number 8) formulates proposals in this area. However, these proposals are made in the context of activities in the laboratory, and the application described does not allow implementation in the production line of an industrial environment. Furthermore, only the detection by Eddy currents is dealt with, which is often inadequate.

The article entitled 'Automatic Detection of Defects in Industrial Ultrasound Images using a Neural Network' by Lawson and Parker (Proc. of Int. Symposium on Lasers, Optics, and Vision for Productivity in Manufacturing I (Vision Systems: Applications), June 1996, Proc. of SPIE vol. 2786, pages 37-47 1996), describes the application of image processing and neural networks to the so-called scan TOFD interpretation. The TOFD (Time of Flight Diffraction) method consists of pinpointing the positions of the ultrasound sensor where it is possible to observe a diffraction of the beam at the edges of the imperfection, which allows subsequent dimensioning of the imperfection. This method is difficult to adapt to existing non-destructive testing equipment, particularly in an industrial environment.

The article entitled 'Shape Classification of Flaw Indications in 3-Dimensional Ultrasonic Images' by Dunlop and McNab (IEE Proceedings—Science, Measurement and Technology—July 1995—Volume 142, Issue 4, pages 307-312) concerns diagnostics in relation to pipeline corrosion. The system allows in-depth non-destructive testing and allows a three-dimensional study in real time. However, the system is very slow. This makes its use in an industrial environment relatively difficult.

The article entitled 'Application of neuro-fuzzy techniques in oil pipelines ultrasonic non-destructive testing' by Ravanbod (NDT&E International 38 (2005), pages 643-653) suggests that the imperfection detection algorithms can be improved by the use of fuzzy logic elements, in combination with the neural network. Here again, however, the techniques studied concern the inspection of pipeline imperfections and diagnosis of corrosion imperfections.

DE 42 01 502 C2 describes a method for creating a signal intended for a neural network but provides little or no information on the interpretation of the results, in diagnostics terms. Furthermore, once again, only detection by Eddy currents is dealt with.

Japanese patent publication 11-002626 concerns the detection of longitudinal imperfections only, and solely by Eddy currents.

Patent publication No. 08-110323 limits itself to a study of the frequency of the signals obtained by ultrasound.

Patent publication No. 2003-279550 describes a program for differentiating between a zone qualified as good and a bad zone of a product using a neural network. This program goes no further, and allows neither the classification nor the localisation of imperfections. As a consequence, the application of this program may frequently lead to the rejection of parts that would be deemed good if the results had been interpreted by a human operator.

Non-Destructive Testing of Pipes—State of the Art

The following detailed description is provided essentially in the context of non-destructive testing of pipes as they leave production, but without this being restrictive.

As indicated in FIG. 1, the imperfections in a pipe T can be identified according to their position. So, surface imperfections, internal or external, include longitudinal imperfections LD, and circumferential (or transverse or crosswise or transversal) imperfections CD and oblique or inclined imperfections ID; by various arrangements of sensors, an attempt is made to detect these as soon as they extend beyond a length and a depth defined according to the standards or specifications or customer requirements (for example, an imperfection length value mentioned in the standards is ½ inch, or approximately 12.7 mm, with a depth of approximately 5% of the thickness of the product tested). Imperfections "in the wall" are also of interest, that is to say in the mass MD (not visible in FIG. 1), which often correspond to inclusions and split ends, the detection of which is attempted at the same time as the thickness measurement. The ultrasound beams are shown diverging in FIG. 1 in order to explain the detection of imperfections. In practice they will be quite convergent, as will be seen.

Conventionally, in non-destructive testing by ultrasounds, one of the following three types of installations is used: so-called 'rotating head' installations, so-called 'rotating pipe' installations, and multi-element encircling sensor installations, all of which are well-known to a person skilled in the art. In the case of the use of sensors that operate by electronic scanning, the relative pipe/sensors rotation is virtual. When used here, the expression 'relative rotation/translation movement between the pipe and the transducer arrangement' covers the case where the relative rotation is virtual.

Figure 2:
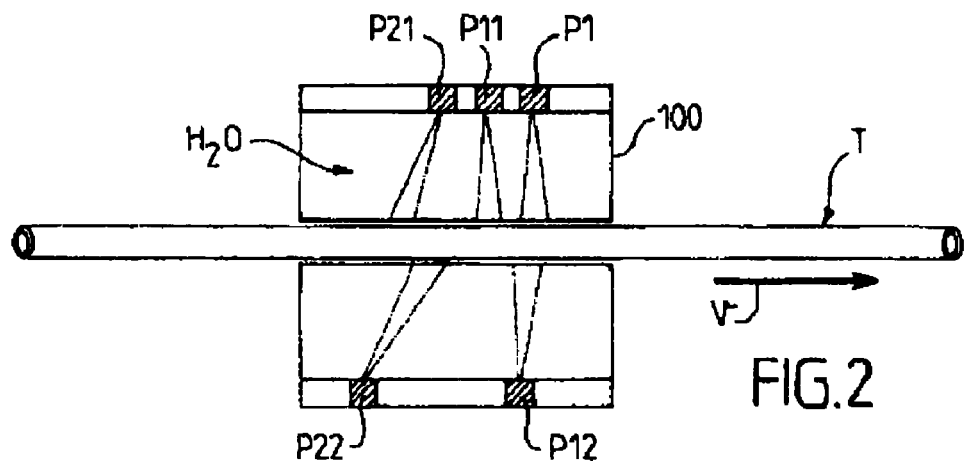
FIG. 2 is a schematic side view illustrating an example of an installation of the "rotating head testing" type on a pipe leaving production.

In FIG. 2, the rotating head non-destructive testing machine comprises an ultrasound device, properly so-called, mounted on a water enclosure, or water box 100, which crosses the pipe T at a speed of v=0.5 metres per second, for example. The ultrasound sensors or probes emit longitudinal waves in the water. A given sensor works, for example, at 1 or a few MHz. It is excited, repeatedly, by pulses of a selected waveform, at a rate (or frequency) of recurrence Fr, also known as pulse repetition frequency (PRF), which is of the order of a few kHz or tens of kHz, for example 10 kHz.

Moreover, an ultrasound transducer has:
a near-field radiation, practically parallel, in a so-called Fresnel zone, home to numerous interferences, whose length along the axis of the beam is $$N=0.25D^2/\lambda$$

where D is the diameter of the active pad of the transducer, and $\lambda$ its working wavelength, and
a far-field radiation, in the so-called Fraunhofer zone, according to a divergent beam of angle $2\alpha$, with $$\sin \alpha = 1.22\lambda/D$$

Figures 3A, 3B, 3C:
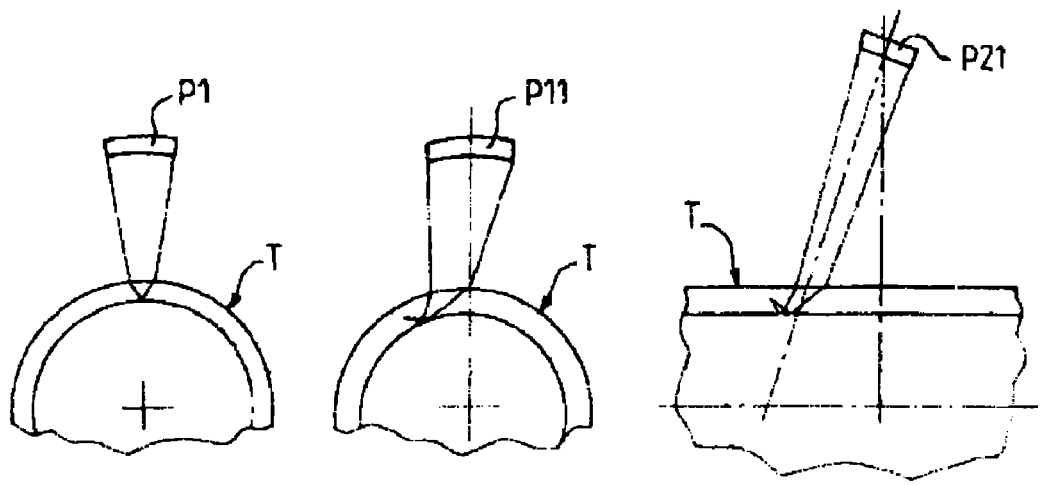
FIGS. 3A to 3C are details of various types of thickness measurement and longitudinal and transverse imperfection testing.

FIGS. 3A, 3B and 3C represent sensors made to converge by means of a concave (ultrasound) lens, as currently used in pipe applications. The Fraunhofer zone is preferably used as there is less disturbance there.

So, for sensors such as P11 and P12, the ultrasound beam, which is generally in focus, extends to the vicinity of a plane perpendicular to the axis of the pipe T. Detection is therefore carried out noticeably in cross-section. Their roles are as follows:
either their beam is also perpendicular to the axis of the pipe T in the cross-section, and they serve to measure the thickness (for example P1, FIG. 3A); this is then referred to as "straight probing";
or their beam has an incidence on the axis of the pipe T, in cross-section, and they serve to detect the longitudinal imperfections (for example P11, FIG. 3B). In this case the angle of incidence in the cross-section is preferably selected in order to generate in the pipe only transversal or shear ultrasound waves, bearing in mind the characteristics of the water/metal interface of the pipe (in principle water/steel). Generally two sensors are provided, P11 and P12, with opposing incidences in relation to the axis of the pipe (FIG. 2).

The machine also comprises sensors such as P21 and P22, the ultrasound beam of which, also in focus, on the other hand extends to the vicinity of a plane passing through the axis of the pipe, but has an incidence in relation to the plane perpendicular to the axis of the pipe T (see sensor P21, FIG. 3C). In this case, the angle of incidence in relation to the plane perpendicular to the axis of the pipe is preferably chosen in order to generate in the pipe only transversal or shear ultrasound waves, bearing in mind the characteristics of the water/metal interface of the pipe (in principle water/steel). These sensors serve to detect the transversal imperfections. Generally two sensors are provided, P21 and P22, with opposing incidences in relation to the perpendicular plane of the axis of the pipe (FIG. 2).

Checking for imperfections generally takes place by focusing the beam. The focal point is measured in relation to the bond, which corresponds to the first outgoing and return trajectory of the ultrasounds in the thickness of the pipe. So, the sensor in FIG. 3A is focused at half-bond, while the sensors of FIGS. 3B and 3C are focused at three-quarters bond. Moreover, the testing for external imperfections generally takes place at the bond, and that for internal imperfections at the half-bond.

Ta is noted, this being the time required for the probe to be able to correctly receive the return ultrasound beam representing a possible imperfection. This time Ta depends on the sum of the following two times:
firstly the outgoing and return propagation time of longitudinal ultrasound waves, over the height of the water column present between the probe and the pipe, along the trajectory of the ultrasounds;
and secondly the propagation time of transversal ultrasound waves, as required within the pipe to perform the non-destructive testing itself. This time depends mainly on the selected number of reflections of the transversal waves within the wall of the pipe.

Conventionally, the probes are made to rotate around the axis of the pipe by means that are not shown, at a speed T of the order of several thousand revolutions per minute (6,000 rpm, for example). In the case, also known to a person skilled in the art, where it is the pipe that is rotated while the probes are not made to rotate (so-called rotating pipe installation), the speed of rotation of the pipe is of the order of between several tens to several thousands of revolutions per minute.

A cell is the name given to each sensor-transmission medium (water)-pipe assembly. For a cell, consideration must also be given to the beam opening Od of the detecting ultrasound probes. An opening can be defined with two components (FIG. 1), one Od1 in the cross-section of the pipe, and the other Od2 in the plane passing through the axis of the pipe and the probe.

Adjustment of the installation (as a function of the speed of rotation, the throughput speed, the dimensions Od1 and Od2 and the number of probes) should guarantee scanning by the ultrasound beams of all the surfaces and volume of the pipe to be tested.

It should be noted that certain standards or customer requirements or specifications state what the coverage of the scanned zones must be.

The analysis time Ta is therefore defined by a compromise between:
the rate (or frequency) of recurrence Fr, also known as pulse repetition frequency (PRF);
in the cross-section of the pipe, the speed of rotation c), taking into account the detection opening Od1 of the ultrasound probes (in other words, bearing in mind the rotation of the sensors, the component Od1 of the beam opening must allow a time for the presence of the imperfection in front of the sensors that is at least equal to Ta);
along the pipe, the speed of throughput v of this, bearing in mind the detection opening Od2 of an ultrasound probe, and the number NFi of probes dedicated to the same function Fi (which therefore constitute a group of probes), around the periphery of the pipe (in other words, bearing in mind the feed of the pipe, the component Od2 of the beam opening must allow a time for the presence of the imperfection in front of the sensor (or the group of sensors) that is at least equal to Ta);
the number of probes dedicated to the same role (that is to say the same function), and
the wave propagation times as defined previously.

Conventionally, the machine typically comprises a total of two sensors such as P11, P12 for testing for LD type and possibly ID type imperfections, two sensors such as P21, P22 for testing for type CD imperfections, plus in principle one sensor of type P1, to measure the thickness of the product and test for type MD imperfections. Each sensor may in fact be a group of sensors working together, as will be seen.

The machine has either integrated or separate excitation and detection electronics associated with each of the sensors. It comprises (FIG. 4) a 70 pulse transmitter, for example at 250 Volts, for excitation of the probe P0 mounted on the water box 100. As an integral part of the non-destructive testing system, the ultrasound probe P0, here a transceiver, receives the echoes following this excitation. Lines 700 and 710 transmit, respectively, the excitation pulse and the signal at the terminals of the probe to an amplifier 73.

The output from the amplifier 73 serves as a display for the operator and/or control of a sorting robot able to separate (downstream) non-conform pipes.

The display is, for example, performed on an oscilloscope 750, which receives as a signal the output from the amplifier 73, and as a time base 752 a signal from a synchronisation stage 753 coming from the transmitter 70. A threshold stage 754 avoids blinding of the oscilloscope at the time of the transmission pulse.

Another output from the amplifier 73 goes to a signal processing stage 760. This processing generally comprises rectification, smoothing and filtering. It is followed by a detection or selector phase 762, capable of isolating significant echoes in a known way. For detection of the imperfection, this is the presence of an echo, with its amplitude or its duration (thus its energy), which are significant, in certain time windows, essentially the half-bond and the bond. For detection of thickness, a check is made that the distance equivalent of the time deviation between the respective bottom echoes correctly corresponds to the desired thickness of the pipe. Anomalies detected according to these criteria can be used to issue an alarm in 764, and/or to control a sorting robot 766 which removes the non-conform pipes, marking these as a function of the anomaly or anomalies detected.

Figure 4:
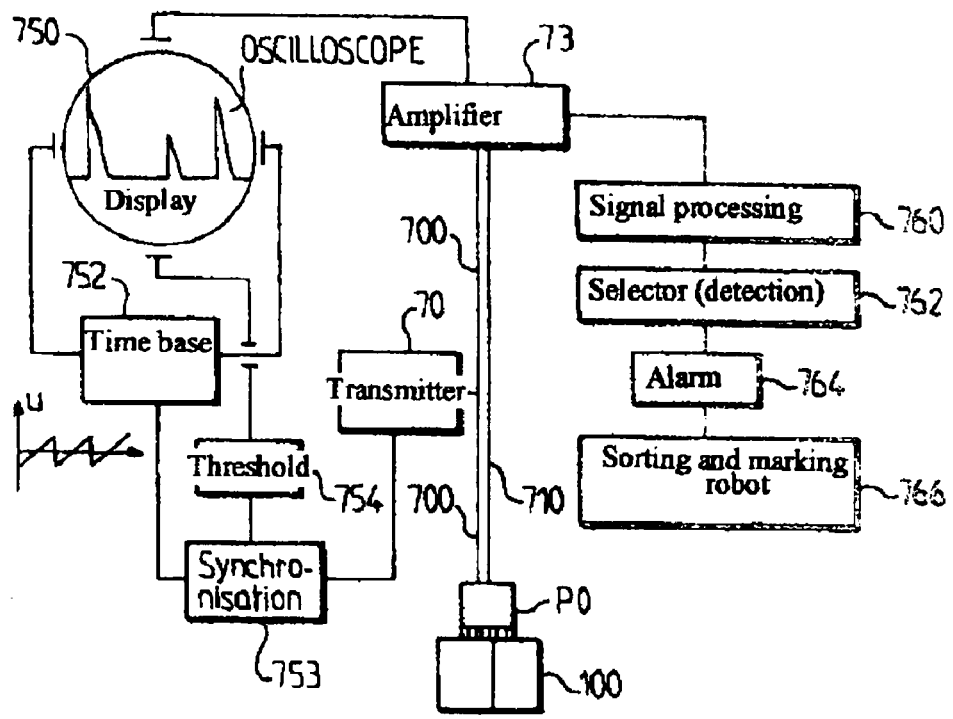
FIG. 4 is the schematic view of the electronics associated with an ultrasound sensor in non-destructive testing in a conventional installation.
Figures 5A, 5B:
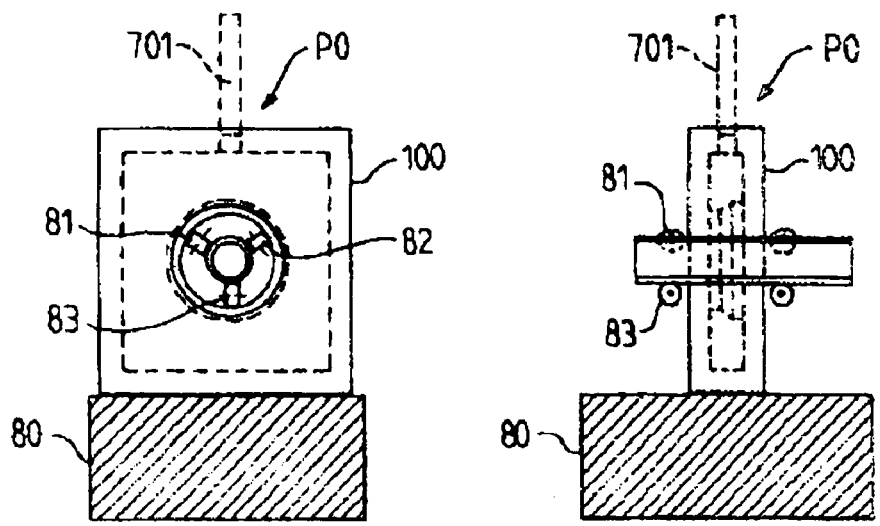
FIGS. 5A and 5B are an end view and a side view of a particular type of non-destructive testing cell, commonly known as a "rotating head" and shown schematically.

Physically in the case of a rotating head installation (FIGS. 5A and 5B), the cell also comprises, on a mechanical support 80, the water box 100, which houses a sensor assembly P0, with a connection 701, that joins the lines 700 and 710 of FIG. 4. Three rolling bearings 81 to 83 are, for example, provided in order to centre the pipe T.

According to the known method (machine sold, for example, by the German company GE NUTRONIK, formerly NUKEM), the sensor assembly P0 comprises sensors that rotate thousands of times per minute around the pipe. A number of sensors can also be used distributed in a ring around the pipe. The ring comprises, for example, 6 sectors of 128 ultrasound sensors, distributed around the periphery. The sensor sectors have an alternating slight offset in the direction of the axis of the pipe. This allows coverage between two consecutive sensor sectors longitudinally and also reduces the problems of interference. Interference occurs when a given sensor receives echoes due to a firing (ultrasonic shot) made on another sensor.

In addition to this there is a bench (not shown) for guiding the pipe upstream and downstream of the non-destructive testing station, in order to accurately position the pipe which passes continuously past the ultrasound sensors.

The non-destructive testing must be performed around the entire periphery of the pipe. But it is also essential that this test monitors the linear speed v of the pipe at the end of production. A compromise is therefore arrived at between the linear speed v of the pipe, the rate (or frequency) of recurrence Fr, also known as pulse repetition frequency (PRF), the analysis time Ta, the working opening Od of the ultrasound probe during detection, and the speed of rotation ω, the number of sensors performing the same function and the speed of propagation of the ultrasound waves.

It is also desirable if the same installation is able to work across a full range of pipe diameters (and also pipe thicknesses), covering the production range. It is then common to provide several values of the speed of rotation ω, and frequency of recurrence Fr, alson known as pulse repetition frequency (PRF), which values are selected as a function of the diameter of the pipe to be processed.

Finally, it will be noted that any change to production will involve a readjustment of the angles of incidence of the ultrasounds of each sensor on the periphery of the pipe. This delicate operation, which is performed manually, currently takes around half an hour, during which time production of pipes is halted. Such are the conditions under which non-destructive testing by ultrasounds of pipes or other profiled and/or thin-walled products as they leave production currently takes place.

In the area of ultrasound non-destructive testing, the following terminology is often employed:

"scan" means a sequence of relative pipe/sensor positions;

"increment" means the scanning pitch (inversely proportional to the frequency of recurrence, also known as pulse repetition frequency (PRF), or the ultrasound firing (shot) frequency);

"Ascan" means the graph of the electrical voltage measured at the terminals of an ultrasound sensor, with time of flight on the abscissa and electrical voltage, also referred to as ultrasound amplitude, on the ordinate;

"Bscan" means an image relative to a given value of the increment, with the scan corresponding to the ultrasound firing (shot) on the abscissa and the time of flight on the ordinate, and at each point the ultrasound amplitude converted to grey scale;

"Echodynamic" means a curve (graph) with an indication on the abscissa of the ultrasound firing (shot) and on the ordinate the maximum amplitude detected in a time selector of the Ascan for the corresponding firing (shot);

"Cscan" means an image with, on the abscissa and the ordinate, the equivalent position in a flat space of the point (scan position) of firing (shot) of the ultrasound wave and representing, converted into grey scale, the maximum ultrasound amplitude for this firing (shot) detected in the time selector considered of the Ascan (image amplitude). In the case of a pipe, a point on the abscissa of the Cscan corresponds to a position on the length of the pipe and a point on the ordinate to a position on the circumference of the pipe. In the case of a flat product, a point on the abscissa of the Cscan corresponds to a position on the length of the flat product and a point on the ordinate to a position on the width of the flat product.

Figure 6:
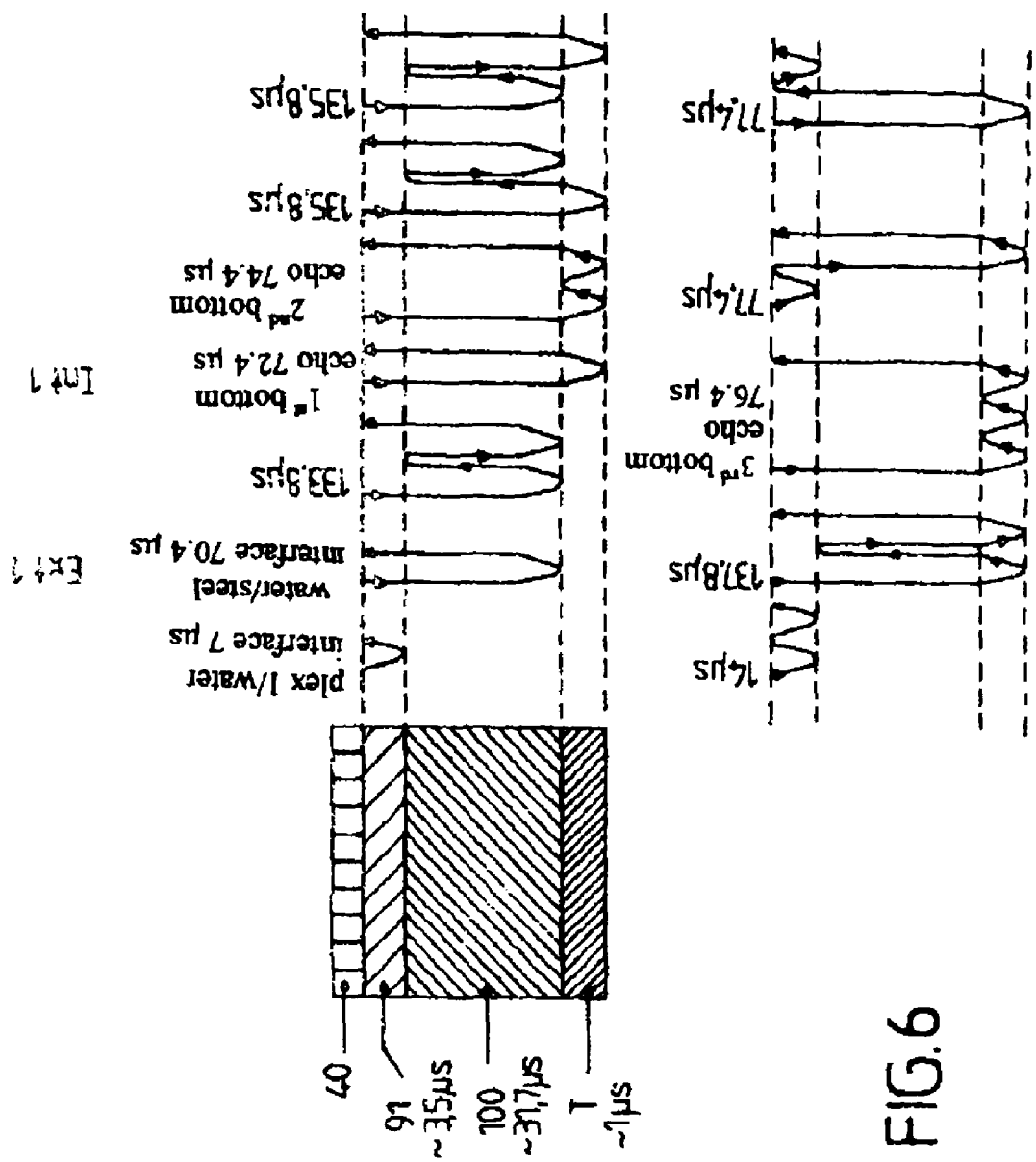
FIG. 6 shows the complexity of the ultrasound trajectories encountered in a pipe, in a simple example.

FIG. 6 is a schematic longitudinal cross-sectional view of a system comprising a sensor, its water column and the pipe, showing the various ultrasound trajectories forming echoes. It allows a good understanding of the complexity of these trajectories and the difficulty of the analysis.

Figure 6A:
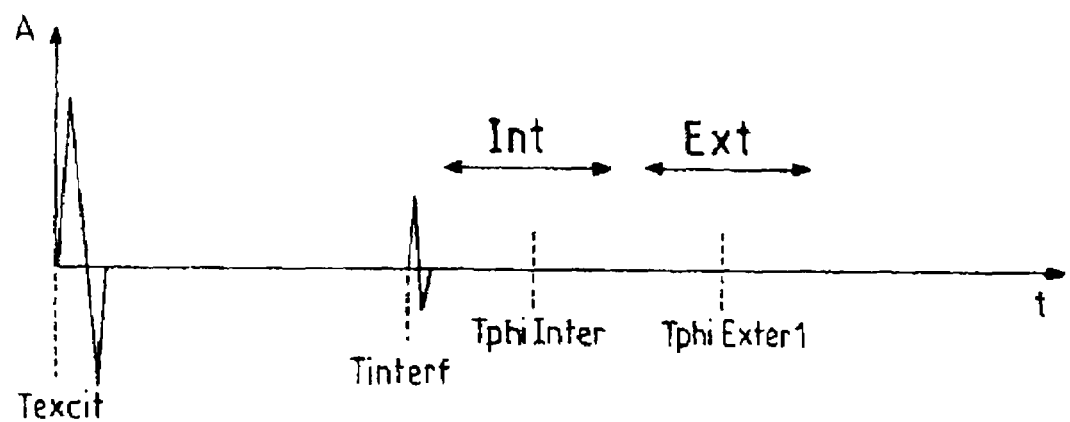
FIGS. 6A and 6B are schematic timing diagrams of ultrasound signals, for a sensor under oblique incidence and for a sensor under normal (perpendicular) incidence, respectively.

FIG. 6A is a schematic amplitude/time diagram of the ultrasound signal at the level of a sensor working under oblique incidence. From the instant Texcit of excitation of the sensor, there is a water-pipe interface echo at the instant Tinterf (which can also be referred to as TphiExter0).

Then there is marking (vertical dotted line) of the instant TphiInter when the ultrasound beam reaches the inner skin of the pipe, where it reflects and refracts, as well as the instant TphiExter1 when the ultrasound beam reaches the outer skin of the pipe. As a result of the oblique incidence, there is no significant reflected echo that returns to the sensor in TphiInter in the absence of an imperfection at this spot. This also applies at TphiExter1.

Figure 6B:
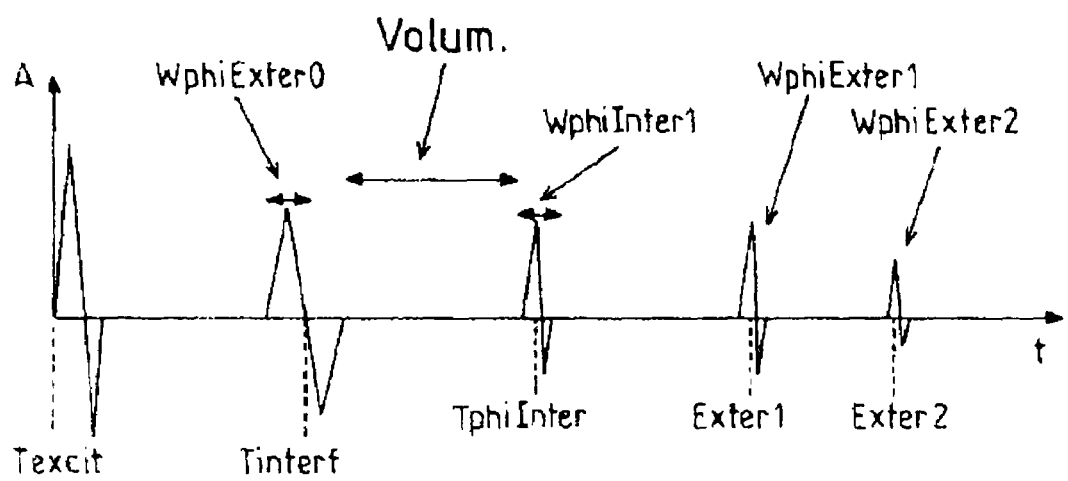

FIG. 6B is a schematic amplitude/time diagram of the ultrasound signal at the level of a sensor working under normal incidence. The general chronology of the signals is the same as for FIG. 6A (except for a factor associated with the incidence). On the other hand, under normal incidence, there are significant echoes in TphiInter and in TphiExter1, even in the absence of an imperfection at the points of the pipe concerned.

The present day non destructive testing systems used in the production of pipes operate by establishing a ratio K between:
  the amplitude As of a signal coming from the pipe to be inspected, and
  the amplitude A0 of the signal coming from a standard reference defect, for the type of test concerned. This "standard reference defect" is in general defined on a reference pipe carrying an artificial defect (for example a U- or V-shaped notch) with selected dimensional characteristics, for example in accordance with a non destructive testing standard and/or customer requirements.

The implied assumption is that this signal amplitude is proportional to the criticality of the imperfection, i.e. to its depth (DD). The graph of FIG. 7 (well known to a person skilled in the art, see Nondestructive Testing Handbook—statistics section of volume 7 published by the ASNT—American Society for Nondestructive testing) represents the real distribution K=f(DD). It shows that in reality the correlation is very poor (of the order of 0.3 to 0.4 for ultrasound testing).

Figure 7:
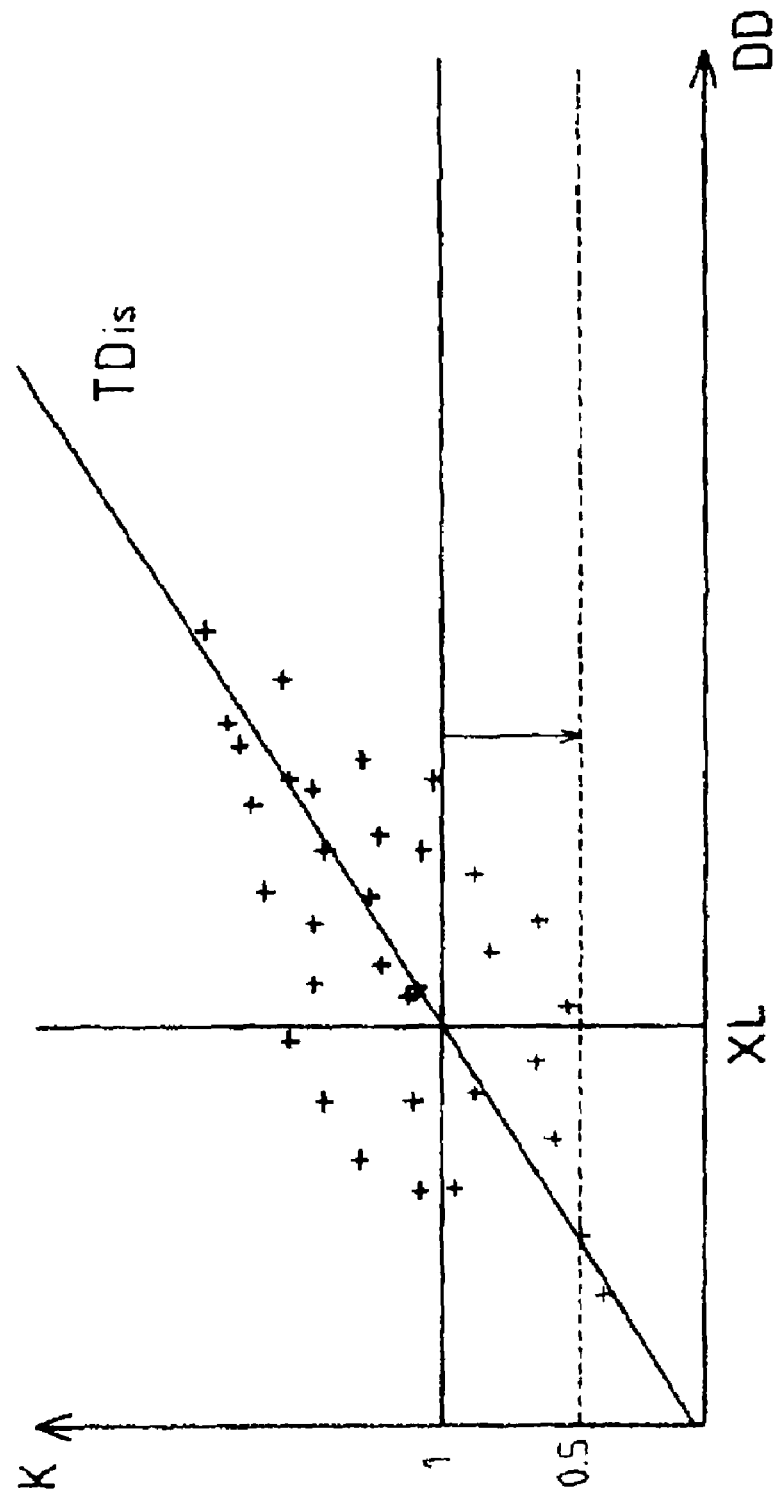
FIG. 7 is a graph showing a conventional representation of the selectivity of a testing installation.

More specifically, in the graph of FIG. 7, if the reference amplitude A0 (K=1) is fixed at the value XL (maximum acceptable depth of imperfection) at the centre of the distribution (itself centred on the oblique TDis), it can be seen that imperfections can still be found at K=0.5 with a depth DD of greater than XL. It follows that, to be on the safe side, it is necessary to set A0 at a much lower value than XL. As a consequence, in production, pipes will be discarded which, however, would in fact be satisfactory. This is all the more disastrous, economically, as pipe manufacture involves heavy engineering and high energy usage.

The applicant has therefore devoted much effort to improving the situation.

Figure 8:
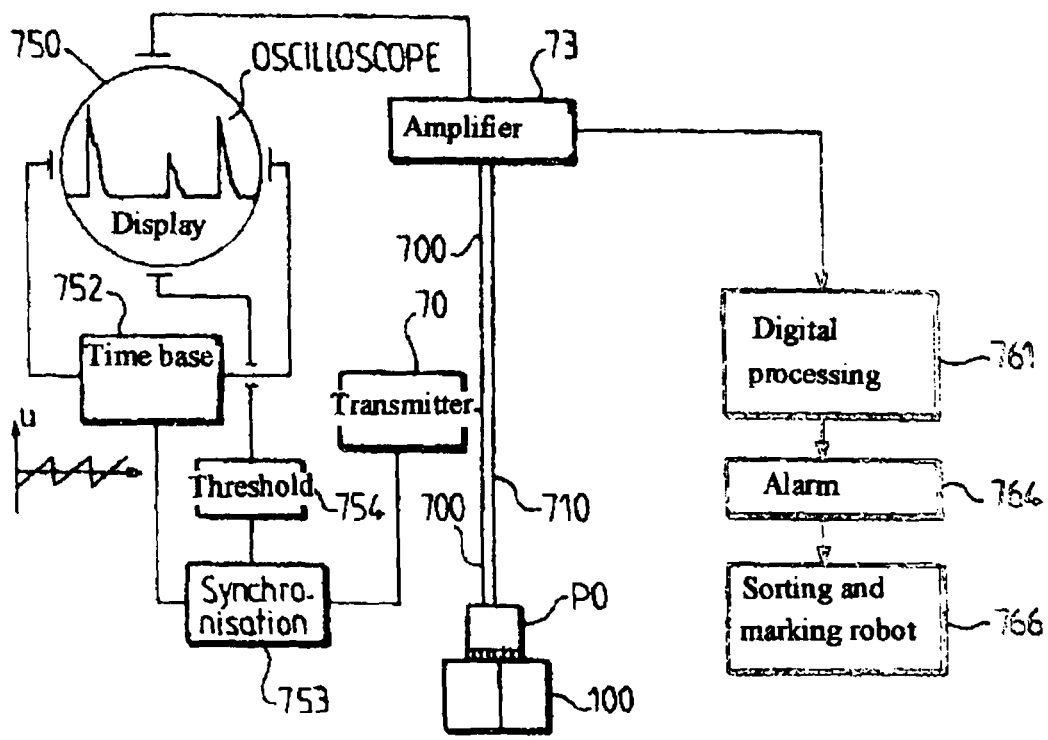
FIG. 8 is a schematic view of the electronics associated with an ultrasound sensor in non-destructive testing in an example of an installation capable of implementing the invention.

FIG. 8 shows a device similar to that of FIG. 4, but modified in order to implement the invention.

The output of the amplifier 73 is applied to a stage 761, which digitises the amplitude of the signal coming from the amplifier 73, and works on this digitised signal. This processing will be described in the following by reference to FIG. 11. Stages 764 and 766 which are functionally similar to those of FIG. 8 can then be retained. The raw signal of the sensor, as can be seen on the oscilloscope 750, is referred to as Ascan by persons skilled in the art. It includes echoes according to the diagram defined by FIG. 6.

It is desirable to perform imaging of the pipe imperfections with the help of ultrasound signals. A description is now provided of how an image is obtained.

In practice an image is obtained by considering several successive scans of the pipe by a sensor Px, under successive angles which roughly cover a cross-section of the pipe. It is possible to do this by successive firings (shots) from a single sensor, using the relative rotation of the pipe/sensor.

By way of example, and without being restrictive, it is a case here of an installation of the so-called rotating head type.

Figure 8A:
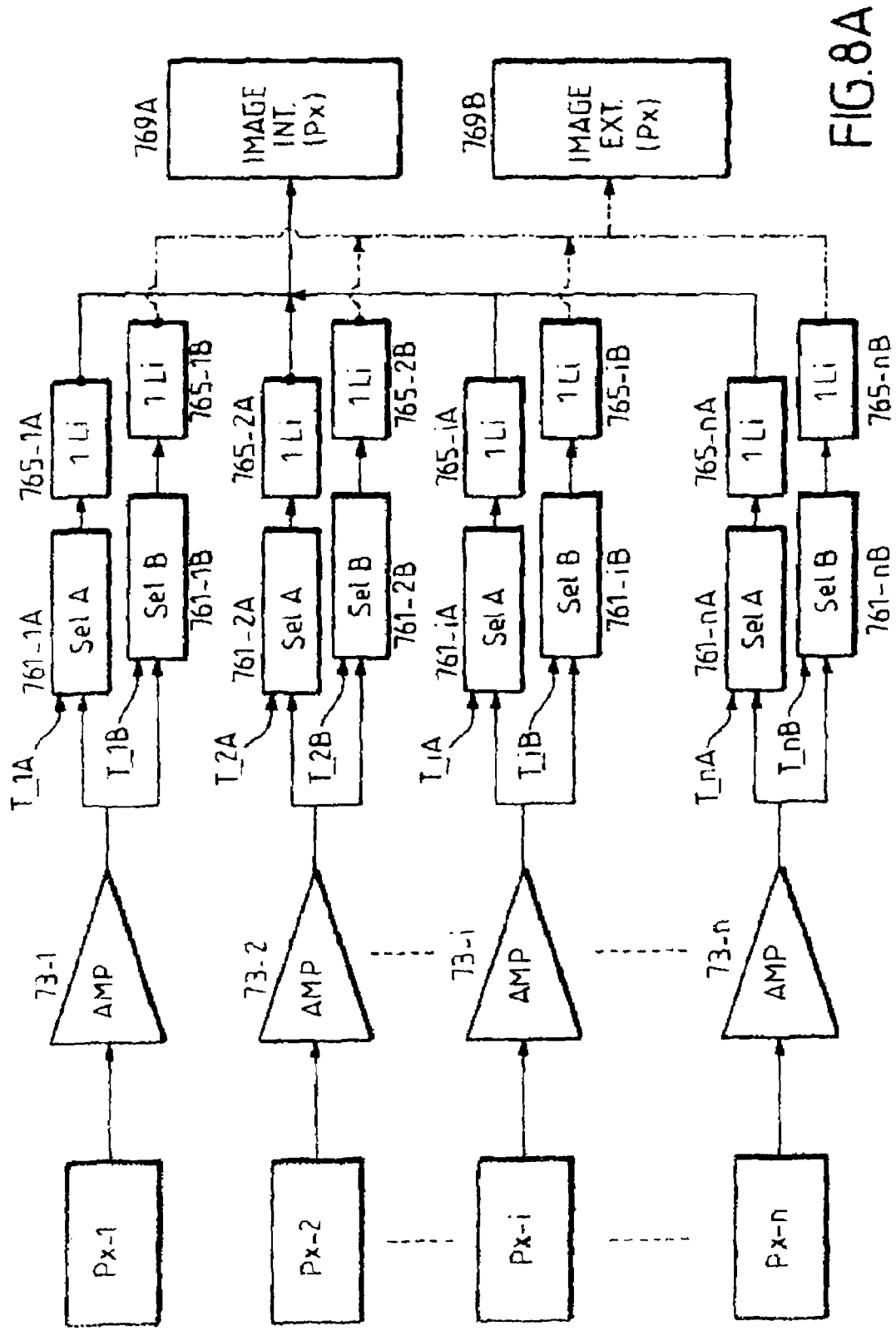
FIG. 8A is a more detailed block diagram of part of FIG. 8.

In FIG. 8A, a sensor Px is considered, which can be one of the types P1, P11, P12, P21 and P22 mentioned above. In the example shown, this sensor Px comprises in fact n elementary sensors Px-1, ..., Px-i, ..., Px-n, which are aligned along the longitudinal axis of the pipe, and which are the object of an ultrasound firing (shot) at the same time. In FIG. 8A, that which is between the elementary sensors and the output images 769A and 769B can be considered to be a converter.

The Ascan signal from the first elementary sensor Px-1 is applied to an amplifier 73-1, followed by two parallel channels: that of selector 761-1A, followed by the digitiser of line 765-1A, and that of the selector 761-1B, followed by the digitiser of line 765-1B.

On the basis of the information obtained as the reference pipe was passed through, the operator enters in the selector 761-1A the information T_1A corresponding to an indication of the position and the time width, which provides it, as a function of the known geometry of the pipe, with the instants where he will find an "inner skin echo", relating to the inside of the pipe, for example the first echo Int1 of FIG. 6. FIG. 6A shows more clearly the corresponding time window "Int", around TphiInter.

Similarly, on the basis of information obtained as the reference pipe was passed through, the operator enters in the selector 761-1B the information T_1B corresponding to an indication of the position and the time width, which provides it, as a function of the known geometry of the pipe, with the instants where he will find an "outer skin echo" relating to the outside of the pipe, for example the first echo Ext1 of FIG. 6. FIG. 6A shows more clearly the corresponding time window "Ext", around TphiExter.

The diagram is repeated for the other sensors Px-2, ..., Px-i, ... Px-n.

So, each time selector 761 works by time windows taking into account the instant of transmission of the ultrasounds, and pre-definable time intervals where there can be expected to be echoes concerning this selector. The illustration of FIG. 6 shows how it is possible to define the time intervals of interest, taking into account the angle of incidence of the ultrasound beam on the pipe, as well as the diameter (internal or external) and the thickness of the pipe. A given time interval corresponds to a given echo at a given point of the pipe, for a given relative position between the pipe and the sensor.

For simplification, it is assumed here that the firing (shot) instants are synchronised with the relative rotation of the pipe/sensors, so that an elementary sensor always works on the same longitudinal generating line of the pipe. The output of its selector thus provides a spaced out succession of analogue signal samples, which each correspond to the amplitude of an echo expected on a wall of the pipe. These samples of sensor Px-1 (for example) are digitised in 765.

Synchronisation with the transmission can be ensured by a link (not shown) with the transmitter 70, or with its trigger, the synchronisation circuit 753, or its time base 752 (FIG. 8). The display 750 can be maintained, if desired. The system can function on a pipe rotating at roughly constant speed. In this case, the angular speed and the feed of the pipe can be measured with the help of an accurate angle encoder, for example model RS0550168 supplied by the Hengstler company, and a laser velocimeter, for example model LSV 065 supplied by the company Polytec. The pipe may also not be rotational, whereas the system of sensors turns. In this case, the laser velocimeter is sufficient for measuring the feed of the pipe, while the speed of rotation of the sensors is known by means of an angle encoder.

For a given firing (shot), all the sensors Px-1 to Px-n provide an image line that corresponds to a cross-section of the pipe. In the other dimension of the image, an elementary sensor provides a line which corresponds to a generating line of the pipe.

The digitisers 765-1A, 765-2A, . . . , 765-iA, . . . , 765-nA allow an "internal" image 769A, relating to the inner skin of the pipe to be filled. The digitisers 765-1B, 765-2B, . . . , 765-iB, . . . , 765-nB allow an "external" image 769B, relating to the outer skin of the pipe (at the output, differing dashes are used to clarify the diagram) to be filled.

The image stored in 769A or 769B, which is a Cscan as defined above, is valid for the sensor or group of sensors Px considered. Each point of this image corresponds, transposed into grey scales, to a value drawn from the amplitude of the echo due to the reflection of the ultrasound signal on a possible imperfection in the pipe zone considered. This value (referred to by K in the following) may represent the relationship between the maximum amplitude of the ultrasound signal captured on the pipe under test and the maximum amplitude of the ultrasound signal obtained with an artificial "standard reference defect", as defined above.

This image now corresponds to a zone of the pipe, obtained by joining together roughly annular zones of the pipe corresponding to each of the digitised lines. In fact, it is a case of annular zones if the ultrasound beam is applied roughly perpendicularly to the axis of the pipe. It is known that the case is different for certain types of imperfections. The zones are then rather more elliptical and, as a result, warped or twisted in space. In the present description, the expression "annular zones" covers these various possibilities.

It should be noted that in order to obtain this complete restoration of the C-scan image, the additional information on the positioning of the pipe in relation to the sensor is required. It is available on a separate input 740. This information comes from an encoder XYZ or a laser XYZ. As the pipe can be likened to a cylinder without any thickness, the positional information can be reduced to two dimensions.

It is understood that the implementation of the invention on an existing ultrasound test bench involves:
- accessibility to the ultrasound testing raw data, which is provided, for example, with the help of a data acquisition card, such as model NI 6024, series E or NI 6251, series M, from the company National Instrument;
- availability of on-line information on the speed of rotation (of the pipe or of the sensor head), and
- availability of on-line information on the pipe feed speed.

The diagram of FIG. 8A can be applied:
- in parallel to a sensor of type P11 and a sensor of type P12, observing the same zone of the pipe from two different directions. Each sensor will allow an internal image 769A, and an external image 769B, to be obtained. Then, one of the images may be selected as a function of a command with the notation "Int/Ext";
- in parallel to a sensor of type P21 and a sensor of type P22, which, here again, will each allow an internal image 769A, and an external image 769B, to be obtained.

The diagram in FIG. 8A can also be applied to a sensor of type P1, in which case three parallel channels are provided behind each amplifier (at least virtually). One of these channels functions in a repetitive time window positioned as indicated under "Volum." in FIG. 6B. This channel allows a check of imperfections in volume, that is to say in the thickness of the pipe.

The two other channels can function respectively in repetitive time windows positioned as shown in "WphiExter0" and in "WphiInter1" in FIG. 6B. These two other channels allow measurement of the thickness of the pipe.

The distinction between the 3 channels is purely functional (virtual). In fact, the aforementioned two other channels can be physically the same, in which there is discrimination of the instants or windows "WphiExter0" and "WphInter1". It is also possible to use a single physical channel, in which there is discrimination of the instants or windows "WphiExter0", "Volum." and "WphiInter1".

It is representative to describe in more detail the case of a sensor of type P11 with a sensor of type P12. This is what will be done now.

It will be recalled that these two groups of sensors P11 and P12 are used for detection of longitudinal imperfections in pipes. Ultrasound testing is performed with ultrasound firings (US shots) in two preferred directions (clockwise-counter-clockwise):
- a sensor or group of sensors P11 provides an ultrasound image of the pipe in a working direction (clockwise);
- a second sensor or group of sensors P12 provides an ultrasound image of the same pipe in another working directions (counter-clockwise).

So the longitudinal imperfections are advantageously detected with 2 sensors or groups of sensors the beam axes of which are inclined symmetrically in relation to a plane perpendicular to the axis of the pipe. The inclination is, for example, approximately +17°. This provides an example of the application of the system with two sensors, or two groups of sensors, as mentioned above.

Figure 9:
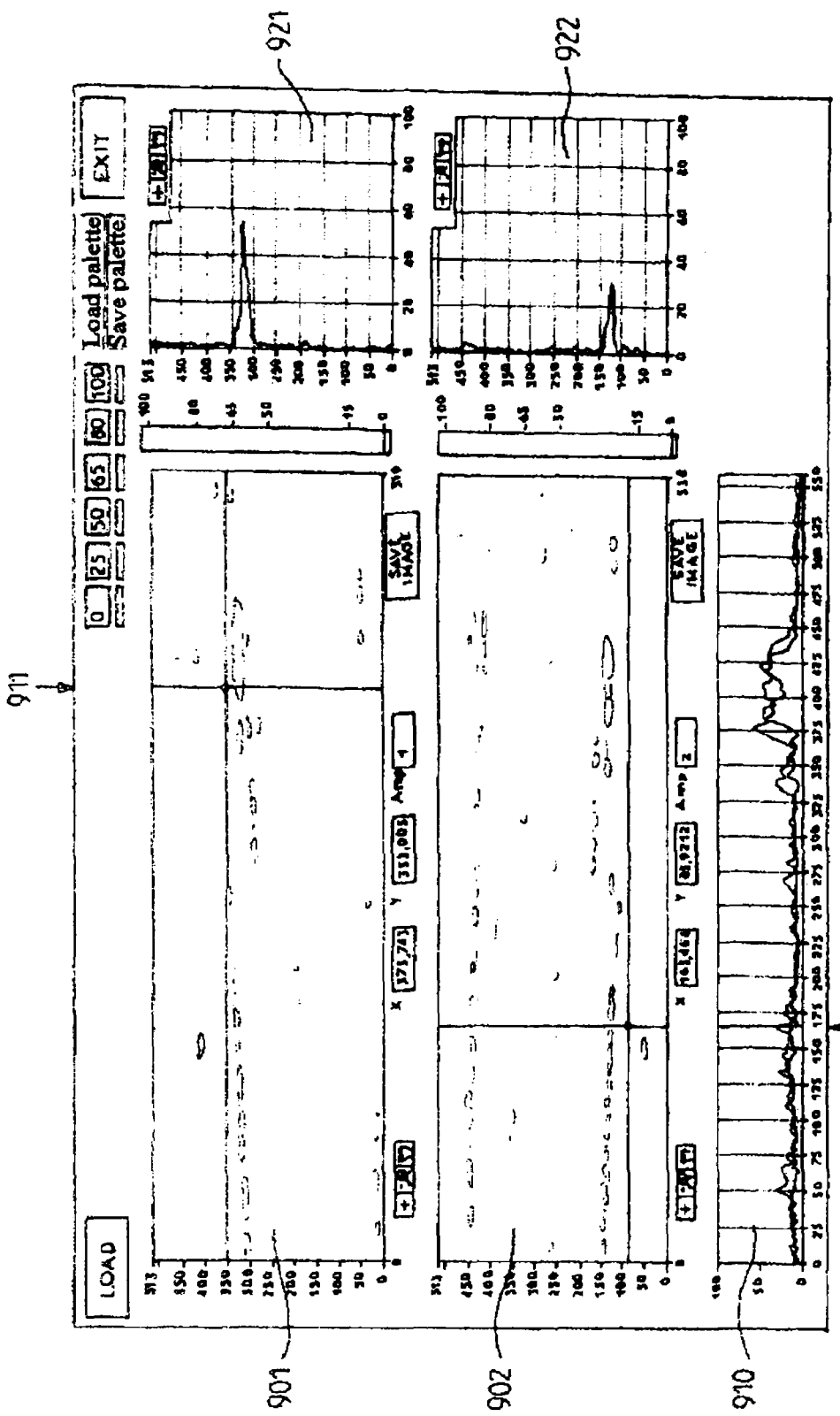
FIG. 9 is a schematised screen shot showing two digitised ultrasound images of potential imperfections in a pipe.
Figure 10B:
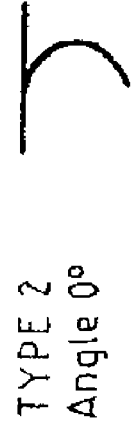
FIGS. 10A to 10D are schematic representations of various types of imperfections according to the American Petroleum Institute (API) classification and which constitute the output data from the neural network tending to determine the type of imperfection.
Figure 10D:
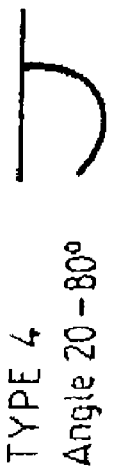
Figure 10A:
Figure 10C:

FIG. 9 is an example of two images 901 and 902 of the C-scan type, one above the other, with the same time reference. These two images come, respectively, from the information from 2 groups of sensors in opposing positions, here the groups of sensors of type P11 and P12 (as a variant the groups of sensors of type P21 and P22) and this for one of the two cases "internal"/"external".

The images of blocks 901 and 902 represent the signal at the grey level (in fact, in a palette of colours). Additional indications are displayed as required, including the supplementary images:
- 921, which is a view of the signal amplitude according to a vertical line 911 selected in image 901;
- 922, which is a view of the signal amplitude according to a vertical line 912 selected in image 902;
- 910, which contains two curves, representing the maximum encountered on the corresponding vertical in the images 901 and 902, respectively.

Figure 11:
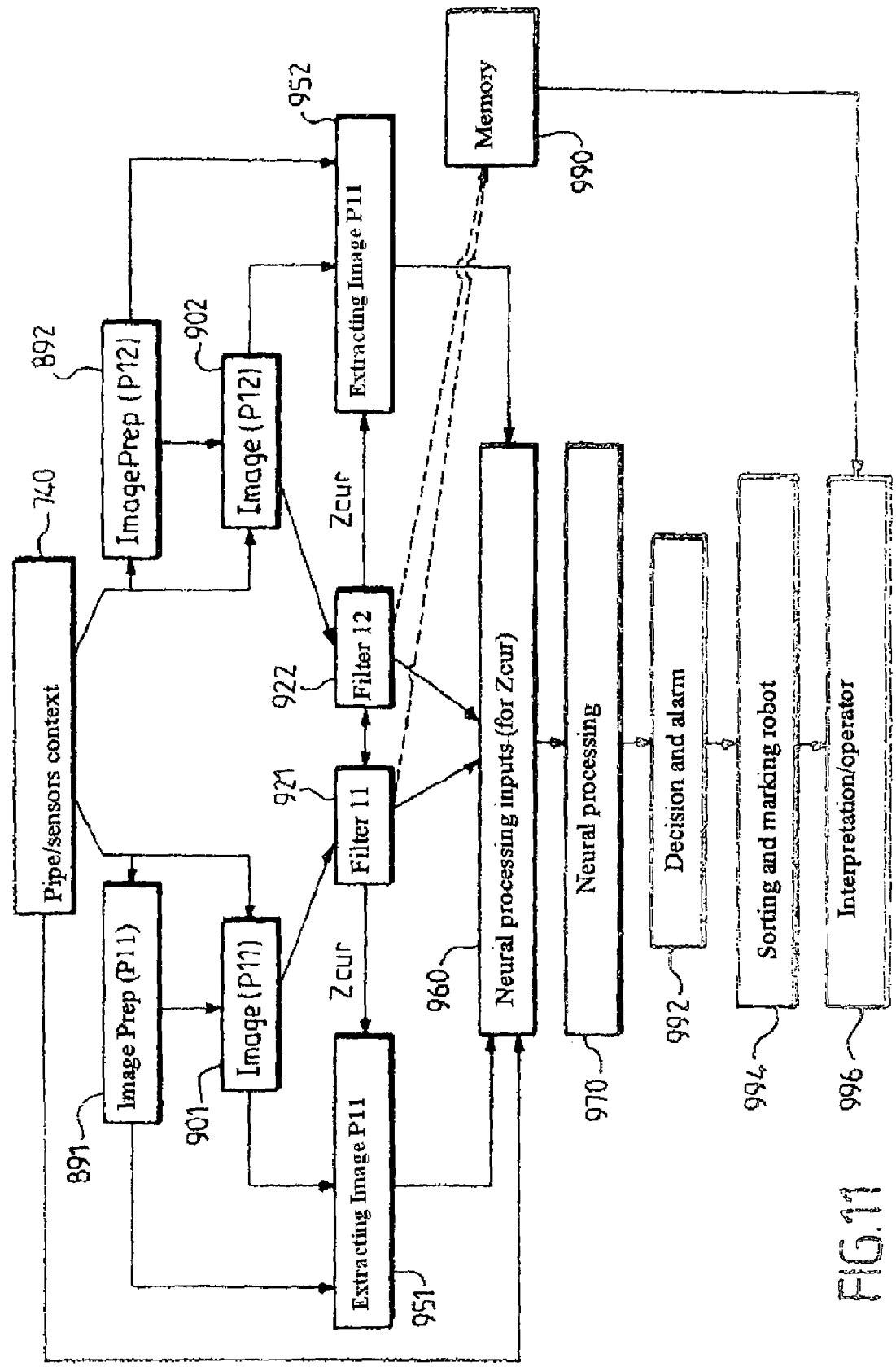
FIG. 11 is a more detailed block diagram of part of FIG. 8.

Reference is now made to FIG. 11. Image blocks 901 and 902 represent the images stored for the sensor groups P11 and P12, for example such as those visible in FIG. 9. Image 901 has been prepared in the way shown in FIG. 8A. The converter block 891 of FIG. 11 corresponds to the setup of FIG. 8A, applied to the sensor P11. Similarly, the converter block 892 also corresponds to the setup of FIG. 8A, but applied to the sensor P12. The converter blocks 891 and 892 use the pipe/sensors contextual data of block 740. These data relate to the characteristics of the pipe under examination and the sensors currently in use. They are also sent to the converter blocks 891 and 892, to the image blocks 901 and 902 and to the combiner block 960.

After blocks 901 and 902, filters 921 and 922 are shown, which in particular allow extracts to be taken from images, and from their preparatory data, as input data combined by the combiner block 960 for neural processing 970, as will be seen.

In the embodiment described, filter 921 has:
- a signal output Zcur designating a working zone in the image. This output is used by an extraction function 951 which as a consequence performs an extraction from the image (Cscan) for the Zcur zone, and an access to the image preparation 891 in order to obtain information stored there (so-called Ascan), relating to the same Zcur zone. All these data are transmitted by the extraction function 951 to the combiner 960, as inputs to the neural processing 970;

an output providing information obtained by filtering, some at least relating to the zone Zcur, which it transmits as input for the neural processing (combiner 960);

optionally (dashed line) additional data outputs to a memory 990.

The same applies to filter 922, with the extraction function 952, for the same Zcur current zone.

The neural processing 970 supplies a decision and alarm circuit 992, which controls a sorting and marking robot 994. An operator interpretation interface 996 can be provided, which can present all or part of the data contained in the memory 990, in relation to the section of pipe under examination.

Here, FIG. 11 deals with information coming from at least two groups of sensors providing the same function or intended for the same type of testing (the 2 groups P11 and P12 or the 2 groups P21 and P22). The same diagram can be used to handle the information coming from a larger number of sensor groups intended for different types of tests. The number of images processed simultaneously is increased by the same amount.

The primary function of the filters 921 and 922 is to determine the imperfection zones in the Cscan images 901 and 902. Generally speaking, the filtering is arranged in order to pinpoint the zones to be analysed and to distinguish there the imperfections from other indications. The filtering works on two equivalent portions of the two images of FIG. 9. In fact, the two filters work together, as indicated by the bidirectional link that joins them in FIG. 11.

By scanning the digital image, to begin with the areas of the image are identified where there are potential imperfections.

To this end it is possible to apply a fixed threshold established by calibration.

The applicant currently prefers to use a threshold that adapts to the prevailing noise level in the image. The method is based on the theory of the detection of a signal in a white noise which can be based on two hypotheses:

Hypothesis H0: measurement=white noise of mean m_b and standard deviation std_b hypothesis H1: measurement=signal+white noise Statistical tests are performed which allow a determination of whether the situations fall within the realm of hypothesis H0 or hypothesis H1. These statistical calculations are performed in real time on n sliding points of the image corresponding to consecutive firings (shots). The number n can be determined by learning.

According to this method (so-called Gaussian addition), it is, for example, possible to use the Neyman-Pearson criterion to determine a detection threshold according to a given probability of false alarm (pfa). This is expressed by the attached formula [21]. The Gaussian cumulative function, generally known as Q (or also the error function erf) is used, which it is necessary to invert in order to obtain the threshold, according to the appended formula [22].

In practice the presence is frequently noted of background noise that may have various origins (for example: presence of water inside the pipe, electrical interference, acoustic phenomena due to the structure of the material of the product under test). The use of a variable threshold avoids the false alarms that occur if a fixed threshold is applied.

Among the other false indications that are likely to appear, interference occurs in the form of very short peaks in the ultrasound signal. This interference can be removed by simple algorithms that can be referred to as cumulative counting algorithms or also integrators (example: "n times before alarm" or "double threshold").

The applicant has also considered the 'turn', which is the trajectory followed by the sensor along the cylindrical surface to which the pipe is likened. Filtering can be performed along each turn in order to further reduce the rate of false alarms. To this end use is made, for example of a Butterworth filter and/or a discrete Fourier transformation, such as a rapid Fourier transformation. This method is applied to each digital line.

The same type of algorithm can be applied in the longitudinal direction of the pipe.

In this way potential imperfections are located. Once an imperfections has been pinpointed its position corresponds to the position analysed in the images of FIG. 9 (for example). This 2D image corresponds to a development of the pipe, likened to a cylinder with no thickness. The radial position/thickness indications (or, more simply, the position of the imperfection internally, externally or in the mass) can be represented as attributes of the points of the image. Thus, we have:

two 2D images representing the possible imperfections in the outer skin of the pipe;

two 2D image representing the possible imperfections in the inner skin of the pipe, and one 2D image representing the possible imperfections in the thickness of the pipe.

The imperfections are now deemed to be "confirmed" following elimination of interference and false alarms, in particular.

Following on from this the applicant has now decided to work on an image zone of fixed size. It is therefore necessary to align this zone with the data on the imperfection existence data that have just been obtained.

In other words, it is necessary to position the points that have been identified as being greater than the threshold in order to determine the complete zone around an imperfection. This is necessary, for example, if it is desired to determine the obliquity of an imperfection.

The algorithm goes through a number of steps:

contour detection (Roberts gradient, for example);

dilation (gathering of near contours);

erosion, then closure, which allow determination of a mask around the imperfections;

a final surrounding stage allowing full localisation of the imperfection.

Thus for each imperfection the coordinates are obtained of the corresponding image zone, which will be useful for the neural network analysis that takes place next.

Figure 12:
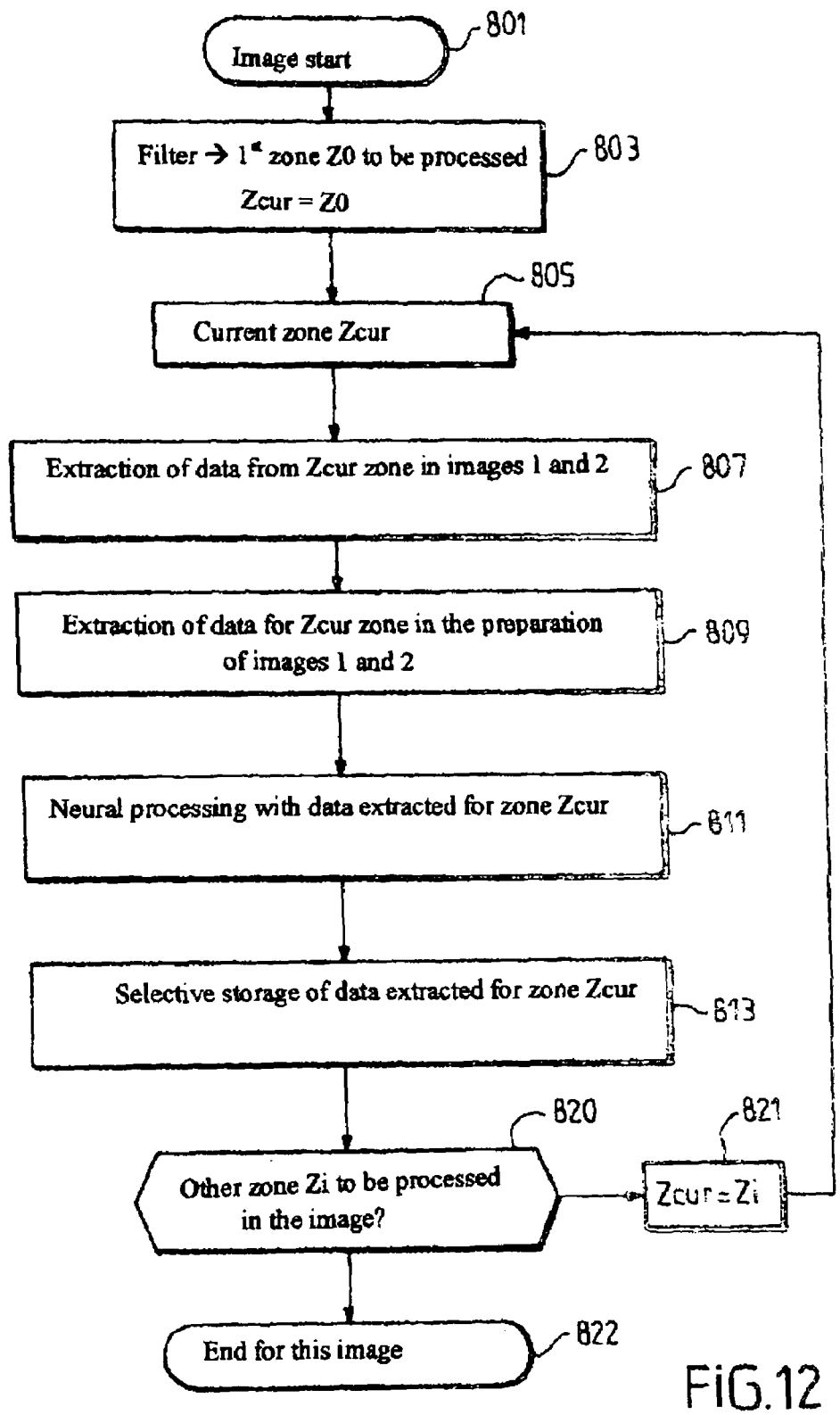
FIG. 12 is a sequence chart illustrating the processing of successive potential imperfections in an image.

FIG. 12 illustrates this processing of the image zones in the form of a flow diagram.

At the start of the images (801), there are between zero and p image zones to be processed representing a confirmed imperfection. Operation 803 assumes that there is at least an initial zone, which serves as the current zone for processing Zcur in 805. For this zone Zcur:

operation 807 selectively extracts data from images 901 and 902 which correspond to this zone (defined by its coordinates in the image);

operation 809 selectively extracts data which have played a part in the preparation of the images 901 and 902, and which correspond to zone Zcur. Examples of these data will be provided below;

operation 811 performs the neural processing properly so-called, more of which later;

the results obtained for zone Zcur are stored selectively in 813, corresponding to a Zcur zone designation;

test 820 looks to see if there is another zone to be processed in the image, in which case a restart is made in 805 with this other zone as indicated in 821; if not, the processing of the current image(s) is terminated (822).

In the case of the processing of sensor P1, there is only one image, which changes the number of input parameters. Apart from this, the processing can generally be the same.

Following determination of each zone of interest Zcur, the filtering can comprise other functions. For these other functions, FIG. 13 illustrates in a schematic way the interaction between the filtering and the series of operations shown in FIG. 11.

Figure 13:
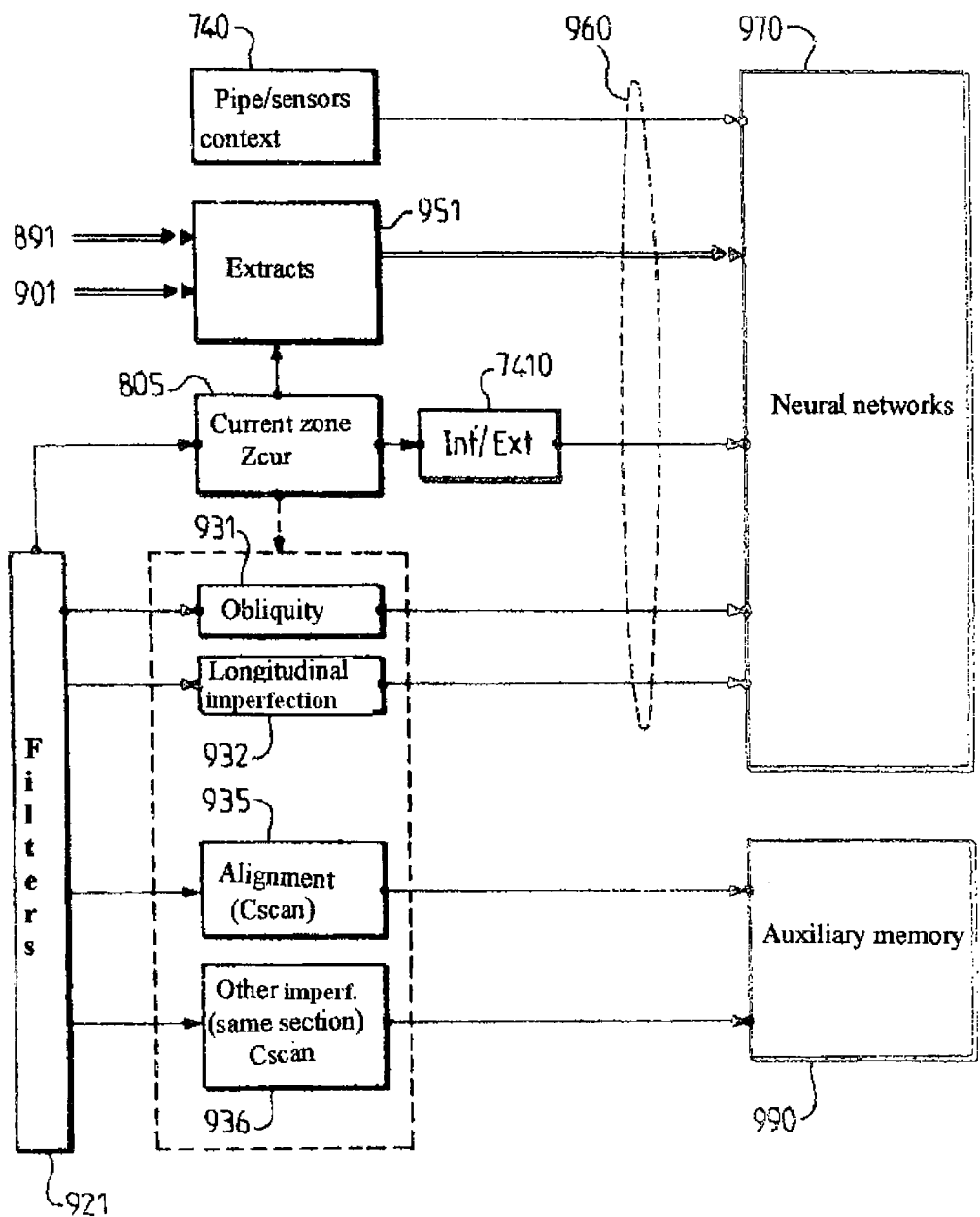
FIG. 13 is a block diagram of a system of filters that can be used according to the invention.

FIG. 13 is similar to FIG. 11, but only for image 901. It shows:

the pipe-sensors contextual elements of block 740;

the extractor 951 which finds the data for the Zcur zone, in image 901 and its preparation 891;

an inner/outer block 7410, indicating if the imperfection in the Zcur zone considered is located in the inner skin or outer skin.

That added to the base data by the filtering is defined in more detail, that is, for each Zcur zone (block 805), as shown by the contents of the box with a dashed line:

investigation of the angle of obliquity in 931;

indication of the length of the imperfection 932.

In addition to the following, in particular, may be included:

an alignment indication in Cscan, in 935, and in 936, an indication of the existence of other imperfections in the same cross-section of the pipe.

In the embodiment described, the data such as 935 and 936 go to memory 990. The remainder goes to the neural networks 970. These are separated there into two functions, as will now be seen.

Neural Circuits

An imperfection in the pipe can be defined by its position, its type and its severity, often likened to its depth. In the embodiment described, the type and degree of depth of a pipe imperfection are determined separately with the help of two neural processes of the same general structure, which will be detailed now using an example.

Figure 14:
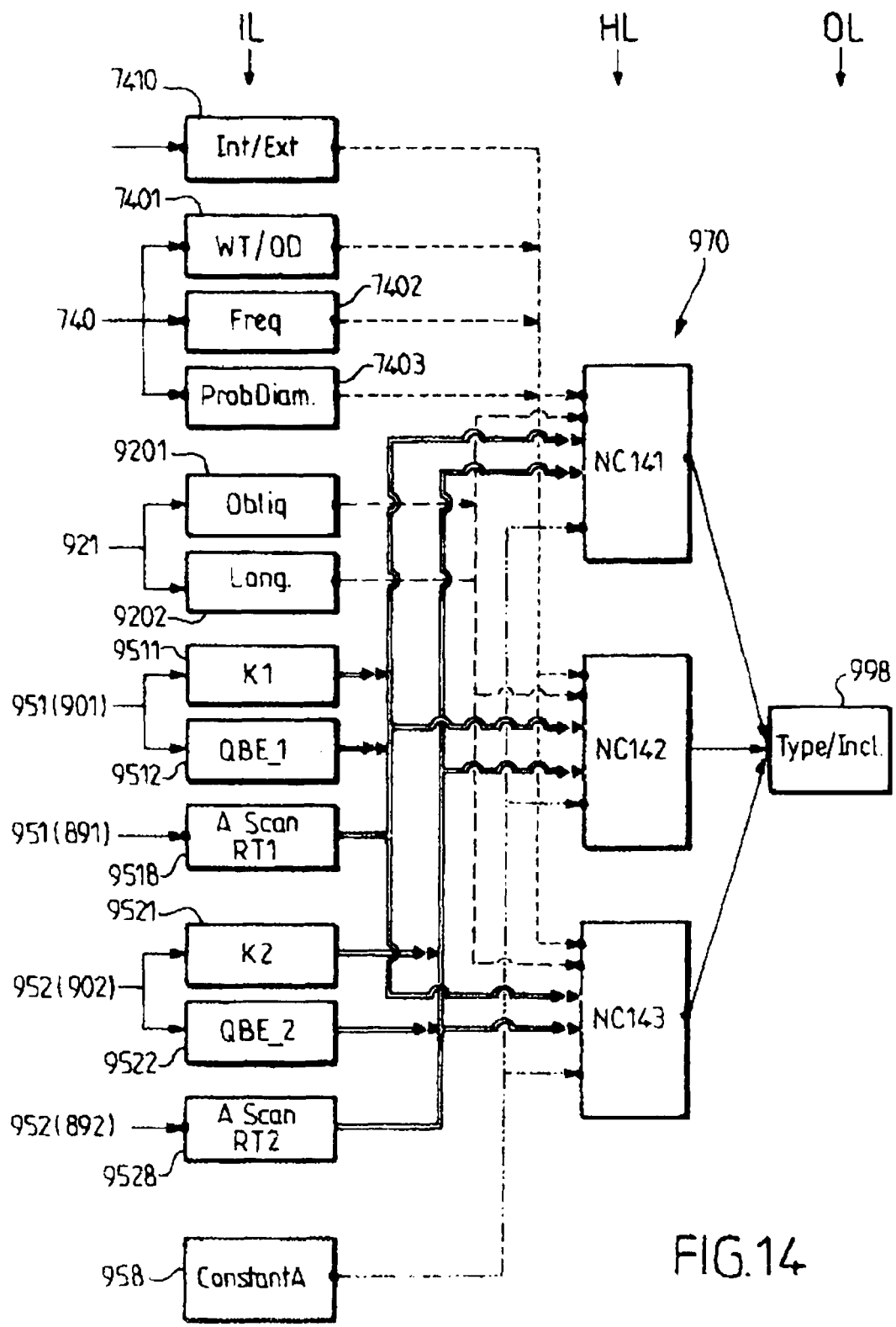
FIG. 14 is a block diagram of a neural network setup tending to determine the type of imperfection in a pipe.
Figure 15:
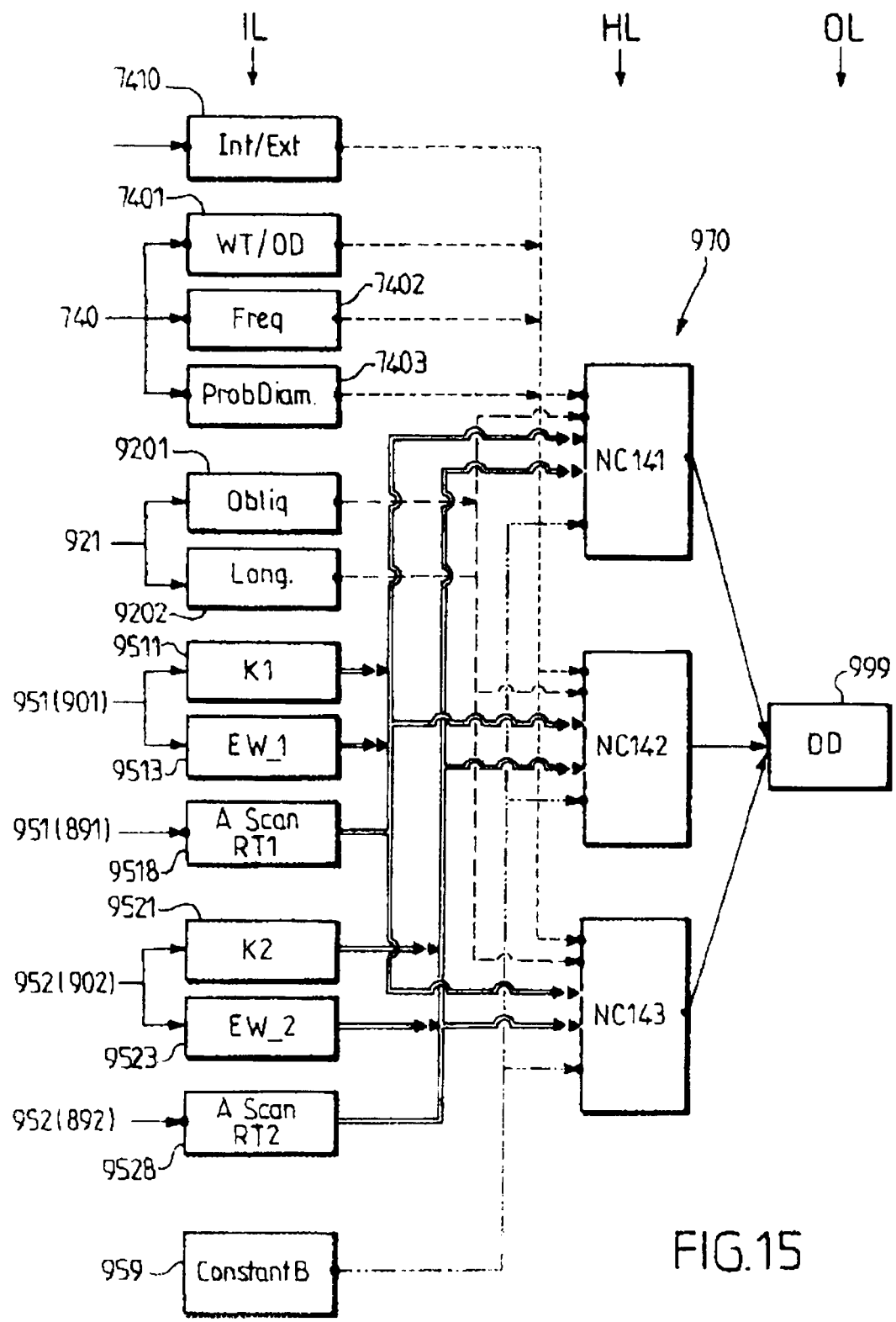
FIG. 15 is a block diagram of a neural network setup tending to determine the degree of depth of an imperfection in a pipe.

The case of the imperfection type is dealt with according to FIG. 14, and that of the severity according to FIG. 15.

The types can be defined, for example as illustrated in FIGS. 10A to 10D. These figures illustrate four types, which represent a simplified choice compared to the list of imperfections supplied by the API and which can be caused by pipe construction processes. The headings in French and English are those used by persons skilled in the art to designate the type of imperfection. It will be noted that imperfections of types 1 and 3 are straight and those of FIGS. 2 and 4 arc-shaped ("chord").

A correspondence between the actual imperfections and the four above types can be defined as follows:

| Name in French | Name in English | Assignment |
|---|---|---|
| Entaille | Notch | TYPE 1 |
| Tapure | Crack | TYPE 1 |
| Paille/repliure perpendiculaire ou droite (laminage) | Seam (perpendicular) | TYPE 1 |
| Paille/repliure (laminage) | Seam (arcuate), | TYPE 2 |

-continued

| Name in French | Name in English | Assignment |
|---|---|---|
| Gravelure | Sliver "overlap" | TYPE 3 |
| Origine billette | Rolled-in-slug | TYPE 4 |
| Rayure | Gouge | TYPE 4 |
| Inclusion | Inclusion | TYPE 4 |
| Manque de matière ("défourni") | Bore-slug | TYPE 4 |
| Chevauchement/recouvrement/repliure | Lap | TYPE 4 |

Here, FIGS. 14 and 15 both use neural circuits with three intermediate neurones (or "hidden neurones"), referred to as NC121 to NC123 for FIG. 14 and NC141 to NC143 for FIG. 15.

FIGS. 14 and 15 have a certain number of inputs in common. As an aid to understanding, the inputs are illustrated using different types of lines. Double lines indicate that the inputs are multiple, that is to say repeated for each point of the Zcur zone.

To begin with, in 7410, according to the status considered by the selectors 761 concerned, information is provided indicating if it is a case of processing an imperfection located in the inner skin or outer skin of the wall of the pipe.

The second category of common input variables includes contextual variables, coming from block 740 (FIG. 13):

in 7401, WT/OD, which is ratio of the wall thickness to the pipe diameter;

in 7402, Freq, which is the frequency of operation of the ultrasound probes;

in 7403, ProbDiam, which is the useful diameter of the ultrasound probes.

The third category of common variables corresponds to the quantities resulting from the filtering, which can be considered common to the two sensors 921 and 922 (or more). An average is taken, for example, of the results from the two sensors, or the most representative result (maximum/minimum, as the case may be) is taken. These quantities are the variables in 9201, the obliquity of the defect, and in 9202 its length. These two variables are easy to pinpoint in the two images of FIG. 9, which have a mirrored symmetry.

Reference is now made to FIG. 14 only. The following category of variables includes variables of different measurements for each of the two sensors (or groups of sensors), and for each of the Zcur zones, which is reflected in the drawing by the use of a double line.

For a first sensor, we have:

in 9511, K1, which is the ratio between the maximum amplitude of the ultrasound signal encountered in the Zcur zone and in image 901, to the maximum amplitude of the abovementioned "standard reference defect". In fact, in the example, the amplitude in each pixel of the image 901 is defined by this ratio; K1 is then simply the amplitude maximum encountered in the Zcur zone of image 901; note Pmax1, the point of the Zcur zone where this maximum is encountered;

in 9512, QBE1 which is a variable of the Cscan referred to as QuantBumpsEchodyn, representing the number of local maxima encountered in the Zcur zone of image 901 in the vicinity of point Pmax1 of maximum amplitude. This number QBE1 is limited to the local maxima encountered in the vicinity of Pmax1, either side, but without the signal amplitude falling below a level corresponding to the background noise. QBE1 will generally take either the value 1 or the value 2.

These two variables come from image 901, via the extractor 951, which is shown by the notation 951(901) in the drawing. Added to this we have:

- in 9518, RT1 which is a variable representing the echo rise time in the native ultrasound signal known as A-scan, (this is the difference between the moment when the signal is at its maximum and the last previous moment when the signal is at the level of the background noise commonly expressed in microseconds). This variable RT1 has previously been measured at the output of the amplifier 73 concerned (FIG. 8A); it has been stored, for example in 891, in correspondence to the point of the pipe to which it relates. It is in this way that it can be selectively retrieved by the extractor 951.

For the second sensor, we have:

- in 9521, K2, which is defined like K1, but for image 902 instead of image 901. In the example, K2 is simply the amplitude maximum encountered in the Zcur zone of image 902; note Pmax2 the point of the Zcur zone where this maximum is encountered;
- in 9522, QBE2 is defined like QBE1, but in image 902 instead of image 901, and in the vicinity of Pmax2. There again, QBE2 will generally take the value 1, or the value 2.

These two variables come from image 902, via the extractor 952. Added to this we have:

- in 9528, RT2 which is a variable representing the echo rise time in the native signal known as A-scan. As before, this variable RT2 has previously been measured at the output of the amplifier 73 concerned (FIG. 8A); it has been stored, for example in 892, in correspondence to the point of the pipe to which it relates. It is in this way that it can be selectively retrieved by the extractor 952.

The final input 958 of the neural network is a constant value, referred to as ConstantA, which represents a constant determined at the time of calibration of the model and resulting from learning.

The output 998 of FIG. 14 is a variable that is indicative of the type of imperfection and its average inclination (defined as a function of the type).

The case of the degree of depth (or severity) of the imperfection is dealt with according to FIG. 15. The inputs are the same as for FIG. 14, except:

- for the first sensor, block 9512 is replaced by a block 9513, which processes a variable EW_1, or EchodynWidth, which is the width at mid-height (50%) of the echodynamic waveform, for this first sensor. This variable EW_1 is drawn from the Cscan;
- similarly, for the second sensor, the block 9522 is replaced by a block 9523, which processes the variable EW_2, or EchodynWidth, which is the width at mid-height (50%) of the echodynamic waveform for this second sensor;
- in 959, the constant, now referred to as ConstantB, is different;
- the output 999 is an indication of the severity of the imperfection, referred to as DD.

Note that, in both cases (FIGS. 14 and 15), a given neural circuit 970 processes an image extract 951 for one of the groups of ultrasound sensors, as well as an image extract 952 corresponding to the same zone, but originating from another group of sensors.

The applicant observed that it was possible to obtain highly satisfactory results, subject to a suitable adjustment of the parameters of the neural circuits, and possibly the number of these, to optimise the prediction.

Moreover, the applicant found that by a combination of the information gathered by the various neural networks, it was possible to further refine the prediction.

Overall, the input parameters of the neural network are then characteristics of the two images (ratio of the max amplitude to the reference amplitude, echo width, orientation of the echo representing the obliquity of the imperfection, etc.) and of the test (sensor, dimensions of the pipe, etc.).

The output parameters are the characteristics of the imperfection (depth, inclination/type). The decision and/or alarm (992) can take place automatically with the help of selected decision criteria, on the basis of thresholds, carrying a degree of safety according to the need. In order to define these thresholds results from the learning can be used.

Figure 16:
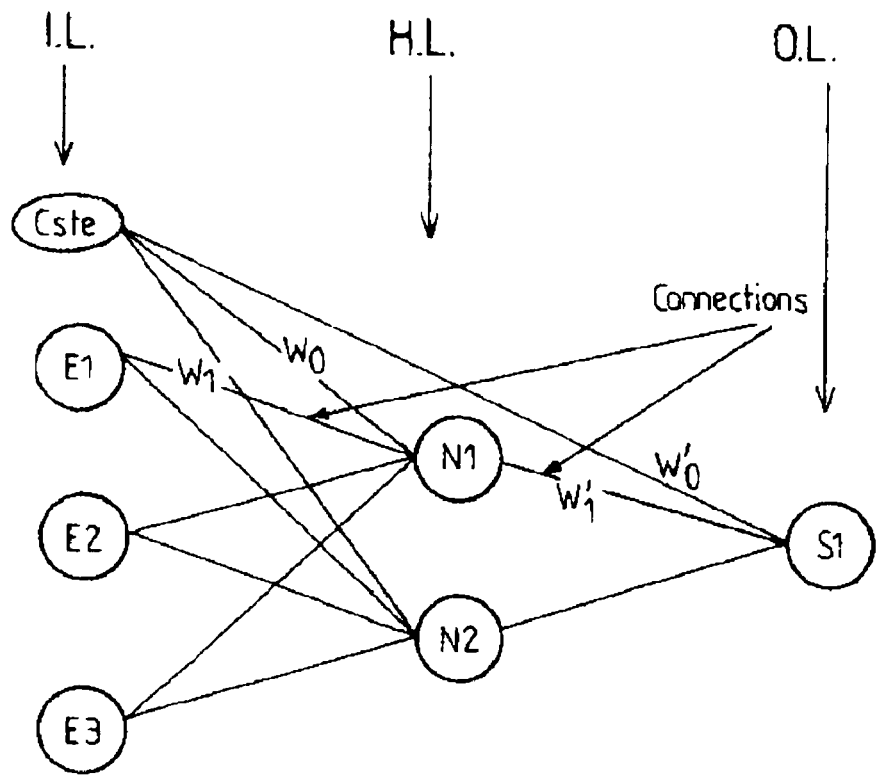
FIG. 16 is a block diagram of the neurone model.

Reference is now made to FIG. 16, which is a model of the elementary neural circuit of FIGS. 14 and 15, for two sensors.

This model comprises an input layer or level IL, which groups together all the input parameters (often called "input neurons"). In order not to overload the diagram, only three neurones E1 to E3 are shown, plus a constant, which can also be considered to be a neuron E0. This constant is most often referred to as the "bias". In practice there are more input neurons, in accordance with FIG. 14 or FIG. 15, as the case may be.

Then at least one hidden layer or level HL is provided, which comprises k neurons (of which only 2 are shown in order not to overload the drawing).

Finally comes the output neurone S1, which provides the decision, in the form of a value representing the importance of an imperfection in the pipe, for example a longitudinal imperfection. This output corresponds to block 998 in FIGS. 14 and 999 in FIG. 15.

Note that the "neuron" constant E0 comes into play to weight not only the hidden layer or layers HL, but also the output neuron (output layer, OL).

The general behaviour of a neural circuit as used here is given by formula [11] of Annex 1, where $w_{ij}$ is the weight assigned to the signal Xi present at the input of neuron j.

Figure 17:
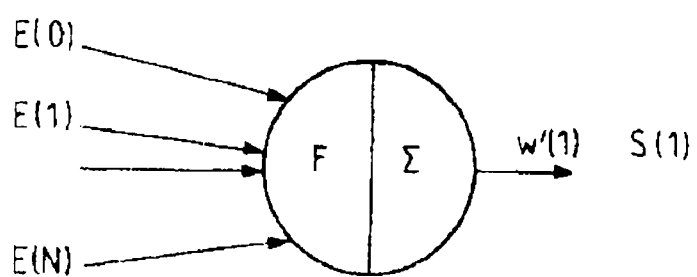
FIG. 17 is an example of an elementary neurone transfer function.

In the circuit provided for here, an elementary neuron behaves according to formula [12], as shown diagrammatically in FIG. 17.

The output S1 of FIG. 16 provides an estimated value that corresponds to formula [13] of Annex 1.

By learning the applicant has adjusted the hidden neurons and their weights such that the function f is a non-linear, continuous, derivable and restricted function. The example currently preferred is the arc-tangent function.

It is known that a neural network determines its coefficients $w_{ij}$, commonly known as synapses, by learning. The learning must typically involve between 3 and 10 times more examples than there are weights to be calculated, while correctly covering the desired range of working conditions.

Starting with examples $E_p$ (p=1 to M), for each example the deviation $D_p$ is determined between the value $S_p$ given by the neural circuit and the actual value $R_p$ measured or defined experimentally. This is what is reflected by formula [14].

The quality of operation of the neural circuit is defined by a global deviation variable Cg, known as "cost". It can, for example, be expressed according to formula [15] as a weighted quadratic global deviation variable.

The learning poses various problems in a case such as that of testing for imperfections in the pipes, in particular due to the fact that heavy engineering is involved, as already indicated.

The applicant first conducted an initial learning by simulation. To this end it is possible to use the CIVA software developed and marketed by the Atomic Energy Agency in France. This initial learning allowed the influencing parameters to be pinpointed and the construction of an initial version of the neural network based on virtual imperfections. The cost function was optimised.

The applicant then conducted a second learning combining the results obtained from simulation and artificial imperfections, that is to say created intentionally on actual pipes. This second learning allowed construction of a second version of the neural network, the cost function of which was also optimised.

The applicant then combined the results obtained with the artificial imperfections, and with a set of imperfections present on actual pipes, these imperfections being known with accuracy from measurements performed a posteriori during the production sequence. This third phase allowed validation of the final version of the neural network. This version has proved itself operationally for production monitoring. However, when implemented in a new or modified installation, it is currently necessary to put it through a "calibration" using around ten artificial samples covering the entire range of imperfections to be dealt with. Of course, an optimisation then follows.

FIGS. 11, 12, 14 and 15 were described in connection with sensors P11 and P12.

The same principle applies to the group of sensors P1. In this case there is no image 2 and the network built has less input parameters, as already indicated. The circuits described for two sensors may be used for just one, but without input parameters for the "Image 2" section.

The same principle can also be applied to the two groups of sensors P21 and P22, in charge of detecting transversal imperfections, bearing in mind that for this detection the sensors are inclined (for example by ±17°) in a plane passing through the axis of the pipe.

It will be understood that, in each case, digital processing takes place of the type defined by FIG. 11, with the exception of elements 992 to 996. This procedure has a global designation, 761, in accordance with FIG. 8 where it is followed by blocks 764 and 766.

Figure 18:
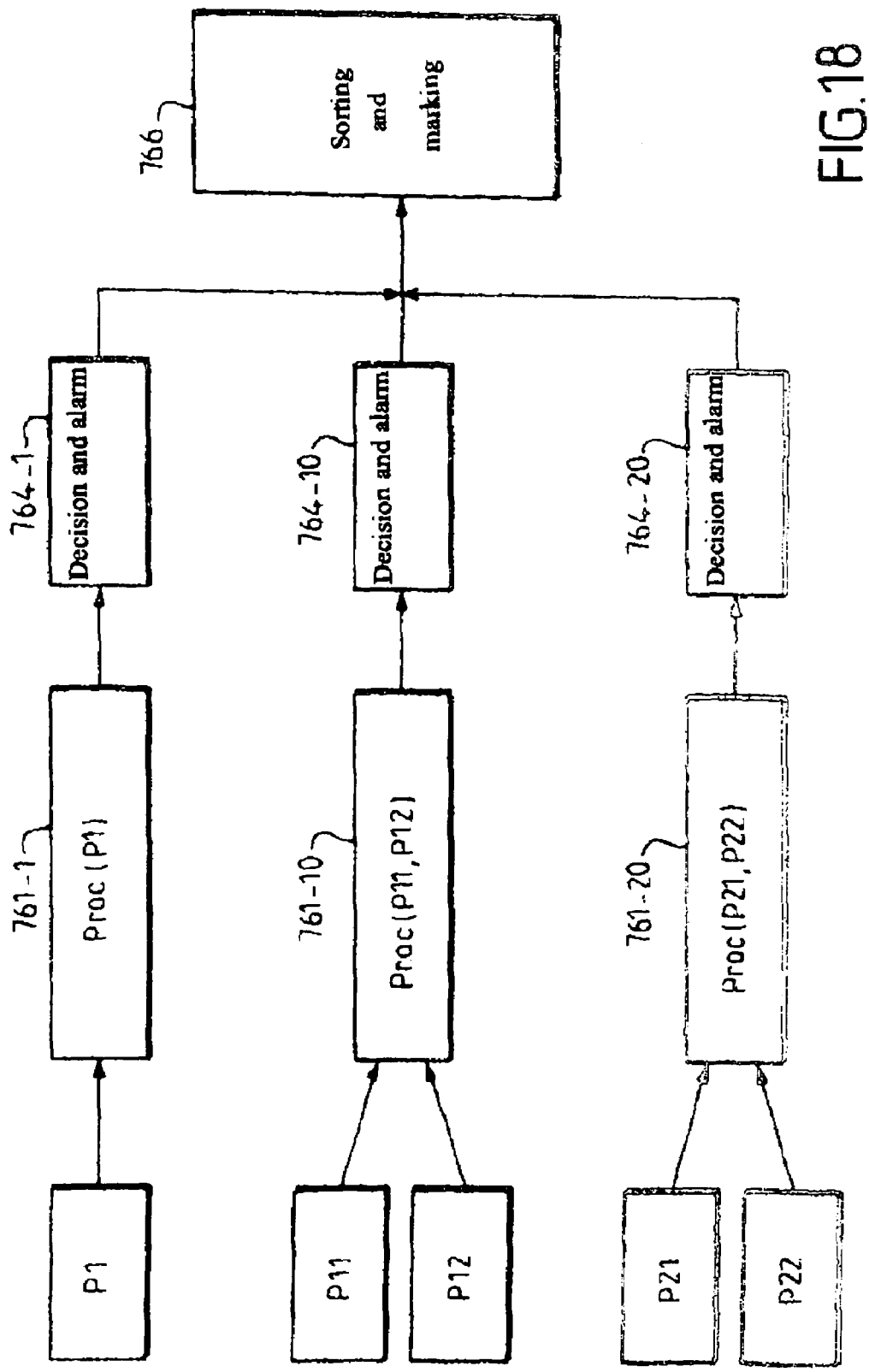
FIG. 18 is the general diagram of an installation using the invention for the detection of defects using various types of sensors.

A set is in this way obtained as shown by FIG. 18, with:
for sensor P1, a procedure 761-1, followed by a decision and alarm phase 764-1;
for sensors P11 and P12, a procedure 761-10, followed by a decision and alarm phase 764-10;
for sensors P21 and P22, a procedure 761-20, followed by a decision and alarm phase 764-20;
the three phases 764-1, 764-10 and 764-20 being interpreted together by the sorting and alarm robot 766.

A variant of FIG. 18, which is not shown, consists of providing only one "decision and alarm" phase, making direct use of the outputs from the three procedures 761-1, 761-10 and 761-20.

The non-destructive testing, properly so-called, takes place "on the fly", that is to say as the pipe passes through the test installation. The decision resulting from the processing of information described above can also be taken either as the pipe passes through the test installation (with decision-alarm and marking "on the fly"); a variant consists in taking this decision once the entire length of the pipe has been inspected, or even at a later time (after testing of an entire batch of pipes, for example), each pipe being referenced/identified (order No. for example). In this case, it is necessary that the information obtained is recorded (stored). The recordings can be the subject of a later analysis by an operator with the authority to take a decision following analysis of the results that have been recorded and processed by the neural networks(s).

Of course, given the properties of the neural circuits, it is possible to combine at least to some extent all the neural networks (contained in procedures 761-1, 761-10 and 761-20) in a single neural circuit having all the desired inputs.

The embodiment described makes direct use of neural networks. The invention is not limited to this type of embodiment. Here the expression "arrangement of the neural circuit type" can cover other non-linear statistical methods with or without neural circuits.

The system proposed here has been described in the case of non-destructive testing in the manufacture of weld-less pipes, a case to which the invention lends itself particularly well. The same methods can apply in particular to elongated iron and steel products which are not necessarily tubular.

In the case of welded pipes or other welded products (such as sheets or plates), the system also proves to be capable of determining the limits of the weld seam, and as a result of locating any imperfections in the weld seam, which it may be necessary to monitor. For their part, imperfections located outside the limits of the weld seam, which may correspond to inclusions already present in the base strip (or product), must be considered differently.

APPENDIX 1

Section 1

$$Y_i = F\left(\sum_j w_{ij} X_i\right) \quad (11)$$

$$S_1 = F\left(\sum_{i=1}^{N} E_i w_i + w_0\right) \quad (12)$$

$$S = \sum_{i=1}^{k} S_i w'_i + w'_0 \quad (13)$$

$$D_p = S_p - R_p \quad (14)$$

$$Cg = \frac{\sum_{p=1}^{p=M} D_p^2}{2M} \quad (15)$$

Section 2

$$pfa = \int_{seuil}^{\infty} \frac{1}{\sqrt{2\pi} \, std_b} e^{-\frac{x-m_b^2}{2std_b^2}} dx = Q\left(\frac{seuil - m_b}{std_b}\right) \quad (21)$$

$$seuil = std_b Q^{-1}(pfa) + m_b \quad (22)$$

$seuil$ = threshold

The invention claimed is:
1. A device forming an operating tool for non-destructive testing during or at an end of production of iron and steel pipes or other elongated products, the operating tool being intended to extract information concerning possible defects in the pipe from feedback signals that are captured following selective excitation of ultrasound transducers according to a selected time rule, the transducers forming a transducer arrangement with a selected geometry, and are mounted in ultrasound coupling with the pipe via an intermediary of a liquid medium, with relative rotation/translation movement between the pipe and the transducer arrangement, said operating tool comprising:

a converter capable of selectively isolating a digital representation of possible echoes in designated time windows as a function of the relative rotation/translation movement and extracting images from the digital representation of possible defects in the pipe;

a filter capable of determining, in the images, presumed defect zones as well as properties of each presumed defect;

a combiner arranged to prepare digital inputs for a neural circuit from an extract of the images corresponding to a presumed defect zone, properties of the presumed defect in the same zone coming from the filter, and contextual data;

at least one neural circuit arrangement that receives the inputs from the combiner, wherein said neural arrangement comprises a first neural circuit suitable for evaluating a nature of a defect among a number of predefined classes, and a second neural circuit suitable for evaluating a seriousness of a defect, wherein the first and second neural circuits have inputs that differ by an input of a number of maxima in a vicinity for the first neural circuit, and an input of an echo width for the second neural circuit;

a digital decision and alarm stage, operating on a basis of an output from the neural circuit arrangement, and a sorting and marking robot, arranged to separate and mark pipes that have been deemed not to conform by the decision and alarm digital stage.

2. A device according to claim 1, intended to work with two arrangements of ultrasound transducers with a selected geometry, mounted in ultrasound coupling roughly according to a mirrored symmetry of a direction of their respective ultrasound beams, wherein said operating tool comprises two converters respectively dedicated to the two arrangements of transducers, and wherein the combiner is arranged to operate selectively on inner skin echoes or on outer skin echoes or echoes taking place in the mass of the pipe, but at the same time on data relating to one or other of the two transducer arrangements.

3. A device according to one of claims 1 and 2, wherein the converter is arranged in order to selectively isolate a digital representation of possible echo maxima in designated time windows corresponding to inner skin echoes, outer skin echoes, and echoes from the mass of the pipe, respectively, and wherein the combiner is arranged to operate selectively on the inner skin echoes or the outer skin echoes or the echoes occurring in the mass.

4. A device according to claim 1, wherein the combiner receives at least one input relating to an amplitude extremum of the image in the presumed defect zone.

5. A device according to claim 1, wherein the filter is arranged in order to produce, as properties of each presumed defect, its obliquity and its length, while the combiner receives corresponding inputs of the defect obliquity and defect length.

6. A device according to claim 1, wherein the filter, the combiner, the neural circuit and the digital decision and alarm stage are arranged to operate iteratively on a series of presumed defect zones, determined by said filter.

7. A device according to claim 6, wherein the filter, the combiner, the neural circuit and the digital decision and alarm stage are arranged to operate alternately on an inner skin and an outer skin of the pipe.

8. A device according to claim 1, wherein outputs of the two neural circuits are combined to refine a prediction of possible defects.

9. A device according to claim 1, wherein the transmission and reception of the ultrasound signals are performed each time by the same transducer, for at least part of the arrangement of transducers.

10. A non-destructive testing device for pipes during or at the end of production, comprising:

an arrangement of ultrasound transducers with a selected geometry, mounted in ultrasound coupling with a pipe via an intermediary of a liquid medium, with relative rotation/translation movement between the pipe and the arrangement of ultrasound transducers;

circuits that selectively excite the transducers according to a selected time rule, and that gather feedback signals the transducers capture, and the operational tool according to claim 1.

11. A non-destructive testing process for iron and steel pipes or other elongated products, during or at an end of production, comprising:

providing an arrangement of ultrasound transducers with a selected geometry, mounted in ultrasound coupling with a pipe via an intermediary of a liquid medium, with relative rotation/translation movement between the pipe and the arrangement of transducers;

selectively exciting the transducers according to a selected time rule;

gathering feedback signals the transducers capture, in order to selectively analyze the feedback signals, so as to extract information on any defects in the pipe;

selectively isolating a digital representation of possible echoes in designated time windows, as a function of the relative rotation/translation movement, and extracting images from the digital representation of possible defects in the pipe;

filtering the images according to selected filter criteria, in order to determine presumed defect zones there, and properties of each presumed defect;

forming working digital inputs from an extract of the images corresponding to a presumed defect zone properties of the presumed defect in the same zone coming from the filter, and contextual data;

applying the inputs so formed to at least one neural circuit arrangement, wherein said neural circuit arrangement comprises a first neural circuit suitable for evaluating a nature of a defect among a number of predefined classes, and a second neural circuit suitable for evaluating a seriousness of a defect, wherein the first and second neural circuits have inputs that differ by an input of a number of maxima in a vicinity for the first neural circuit, and an input of an echo width for the second neural circuit;

digitally processing output from the neural circuit arrangement according to selected decision criteria in order to provide a decision and/or an alarm, and separating and marking pipes considered not to conform by the digitally processing the output.

12. A process according to claim 11, wherein:

at the step of providing an arrangement of ultrasound transducers with a selected geometry, two arrangements of ultrasound transducers with a selected geometry are provided for, mounted in ultrasound coupling roughly according to a mirrored symmetry of a direction of their respective ultrasound beams, wherein the steps of selectively isolating a digital representation of possible echoes, filtering the images, forming working digital inputs, applying the inputs, digitally processing output from the neural circuit arrangement, and separating and marking pipes are performed jointly on signals coming from the two arrangements of transducers.

13. A process according to one of claims 11 and 12, wherein:
in the step of selectively isolating a digital representation of possible echoes, said designated time windows comprise at least some of the windows of the group corresponding to inner skin echoes, outer skin echoes and echoes from the mass of the pipe.

14. A process according to claim 11, wherein:
in the step of filtering the images, the filtering criteria selected comprise at least a defect existence criterion, a defect obliquity criterion and a defect length criterion.

15. A process according to claim 11, wherein:
the steps of forming working digital inputs and applying the inputs are repeated iteratively for each defect detected at the step of filtering the images.

* * * * *